(12) United States Patent
Baurin et al.

(10) Patent No.: US 9,382,312 B2
(45) Date of Patent: Jul. 5, 2016

(54) HUMANIZED ANTIBODIES SPECIFIC TO THE PROTOFIBRILLAR FORM OF THE BETA-AMYLOID PEPTIDE

(71) Applicant: SANOFI, Paris (FR)

(72) Inventors: Nicolas Baurin, Arpajon (FR); Francis Blanche, Paris (FR); Beatrice Cameron, Paris (FR); Marc Duchesne, Sucy en Brie (FR); Vincent Mikol, Charenton-le-Pont (FR); Souad Naimi, Saint Maur des Fosses (FR); Laurent Pradier, Verrieres (FR); Yi Shi, Paris (FR)

(73) Assignee: Sanofi, Paris (FR)

(*) Notice: Subject to any disclaimer, the term of this patent is extended or adjusted under 35 U.S.C. 154(b) by 165 days.

(21) Appl. No.: 14/042,942

(22) Filed: Oct. 1, 2013

(65) Prior Publication Data
US 2014/0105890 A1 Apr. 17, 2014

Related U.S. Application Data

(62) Division of application No. 13/319,710, filed as application No. PCT/FR2010/050915 on May 11, 2010, now Pat. No. 8,614,299.

(30) Foreign Application Priority Data
May 12, 2009 (FR) ..................... 09 53133

(51) Int. Cl.
*A61K 39/395* (2006.01)
*C07K 16/18* (2006.01)

(52) U.S. Cl.
CPC ............ *C07K 16/18* (2013.01); *A61K 39/3955* (2013.01); *C07K 2317/24* (2013.01); *C07K 2317/33* (2013.01); *C07K 2317/52* (2013.01); *C07K 2317/56* (2013.01); *C07K 2317/565* (2013.01)

(58) Field of Classification Search
CPC ............ C07K 16/18; C07K 2317/52; C07K 2317/33; C07K 2317/24; C07K 2317/56; C07K 2317/565; C07K 2317/51; C07K 2317/515; C07K 2317/76; C07K 2316/96; A61K 39/3955
See application file for complete search history.

(56) References Cited

U.S. PATENT DOCUMENTS

| | | | |
|---|---|---|---|
| 5,530,101 | A | 6/1996 | Queen et al. |
| 5,565,332 | A | 10/1996 | Hoogenboom et al. |
| 5,585,089 | A | 12/1996 | Queen et al. |
| 6,750,324 | B1 | 6/2004 | Schenk et al. |
| 6,761,888 | B1 | 7/2004 | Schenk |
| 7,179,463 | B2 | 2/2007 | Lannfelt et al. |

FOREIGN PATENT DOCUMENTS

| | | | |
|---|---|---|---|
| CH | WO 2008081008 A1 * | 7/2008 | ............ C07K 16/00 |
| EP | 0239400 | 9/1987 | |
| EP | 0519596 A1 | 12/1992 | |
| EP | 0592106 A1 | 4/1994 | |
| WO | WO 91/09967 | 7/1991 | |
| WO | WO 97/09351 | 3/1997 | |
| WO | WO 02/46237 A2 | 6/2002 | |
| WO | WO 2005/123775 A1 | 12/2005 | |
| WO | WO 2006/081171 A1 | 8/2006 | |
| WO | WO 2007/108756 A1 | 9/2007 | |
| WO | WO 2009/032661 | 3/2009 | |
| WO | WO 2009/065054 A2 | 5/2009 | |

OTHER PUBLICATIONS

Janson J et al. (2004) Increased risk of type 2 diabetes in Alzheimer disease. Diabetes, 53:474-481.*
Lee EB et al. (2006) Targeting amyloid-beta peptide (Abeta) oligomers by passive immunization with a conformation-selective monoclonal antibody improves learning and memory in Abeta Precursor Protein (APP) transgenic mice. J. Biol. Chem. 281(7):4292-4299.*
Mamikonyan G et al. (2007) Anti-Abeta 1-11 antibody binds to different beta-amyloid species, inhibits fibril formation, and disaggregates preformed fibrils but not the most toxic oligomers. J. Biol. Chem. 282(31):22376-22386.*
Tsuno N & Homma A (2009) What is the association between depression and Alzheimer's disease? Expert Rev. Neurother. 9(11):1667-1676.*
International Search Report WO2010/130940 dated Nov. 18, 2010.
Angal, et al., A Single Amino Acid Substitution Abolishes the Heterogeneity of Chimeric Mouse/Human (IgG4) Antibody, Molecular Immunology, vol. 30, No. 1, (1993), pp. 105-108.
Duyckaerts, et al., Diagnosis and Staging of Alzheimer's Disease, Neurobiology of Aging, vol. 18, S4, pp. 33-42, (1997), pp. S33-S42.
Jellinger, et al., Neuropathology of Alzheimer's Disease: A Critical Update, J. Neural Transmission Supp. vol. 54, (1998), pp. 77-95.
Lazar, et al., A Molecular Immunology Approach to Antibody Humanization and Functional Optimization, Molecular Immunology. vol. 44, (2007), pp. 1986-1998.
Padlan. et al., A Possible Procedure for Reducing the Immunogencity of Antibody Variable Domains While Preserving Their Ligand-Binding Properties. Molecular Immunology. vol. 28, No. 4/5. (1991), pp. 489-498.
Racke, et al., Exacerbation of Cerebral Amyloid Angiopathy-Associated Microhemorrhage in Amyloid Precursor Protein Transgenic Mice by Immunotherapy is Dependent on Antibody Recognition of Deposited Forms of Amyloid Beta, J. of Neuroscience, vol. 25, No. 3, Jan. 19, 2005, pp. 629-636.
Ratovsky, et al., Choosing Near-Linear Parameters in the Four-Parameter Logistic Model for Radioligand and Related Assays, Biometrics, vol. 42, (1986), pp. 575-582.

(Continued)

*Primary Examiner* — Kimberly A. Ballard
(74) *Attorney, Agent, or Firm* — Lathrop & Gage LLP; James H. Velema, Esq.

(57) ABSTRACT

The present application relates to humanized antibodies specific to the protofibrillar form of the beta-amyloid peptide, and to the use of said antibodies in the field of Alzheimer's disease.

26 Claims, 8 Drawing Sheets

(56) References Cited

OTHER PUBLICATIONS

Roguska, et al., Humanization of Murine Monoclonal Antibodies Through Variable Domain Resurfacing, PNAS. vol. 91, (1994), pp. 969-973.

Schmitz, et al., Hippocampal Neuron Loss Exceeds Amyloid Plaque Load in a Transgenic Mouse Model of Alzheimer's Disease. Am J. of Pathology, vol. 164, No. 4, (2004); pp. 1495-1502.

Schupf, et al., Peripheral ABeta Subspecies as Risk Biomarkers of Alzheimer's Disease, PNAS, vol. 105, No. 37, (2008), pp. 14052-14057.

Studnicka, et al., Human-Engineered Monoclonal Antibodies Retain Full Specific Binding Activity by Preserving Non-CDR Complementarity-Modulating Residues, Protein Engineering, vol. 7, No. 6, (1994), pp. 806-814.

Yanker, B., New Clues to Alzheimer's Disease: Unraveling the Roles of Amyloid and Tau, Nature Medicine, vol. 2, No. 8, (1996), pp. 850-853.

MacCallum, et al., Antibody-Antigen Interactions: Contact Analysis and Binding Site Topography, (1996), J. Mol. Biol., vol. 262, pp. 732-745.

Padlan, et al., Structure of an Antibody-Antigen Complex: Crystal Structure of the HyHEL-10 Fab-Lysozyme Complex, (1989). Proc. Natl Acad Sci USA, vol. 86, pp. 5938-5942.

Paul, WE (editor), Fundamental Immunology. Third Edition, Raven Press, NY, (1993), pp. 292-295.

Rudikoff, et al., Single Amino Acid Substitution Altering Antigen-Binding Specificity, (1982), Proc Natl Acad Sci USA, vol. 79, No. 6, pp. 1979-1983.

Vajdos, et al., Comprehensive Functional Maps of the Antigen-Binding Site of an Anti-ErbB2 Antibody Obtained With Shotgun Scanning Mutagenesis, (2002), J. Mol. Biol., vol. 320, No. 2. pp. 415-428.

\* cited by examiner

SEQUENCE LISTING

```
<160> NUMBER OF SEQ ID NOS: 32

<210> SEQ ID NO 1
<211> LENGTH: 1326
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(1326)

<400> SEQUENCE: 1 gag gtc cag ctg cag cag tct ggg cct gag gtg gtg aag cct ggg gtc      48
Glu Val Gln Leu Gln Gln Ser Gly Pro Glu Val Val Lys Pro Gly Val
1               5                   10                  15 tca gtg aag att tcc tgc aag ggt tcc ggc tac aca ttc act gat tat      96
Ser Val Lys Ile Ser Cys Lys Gly Ser Gly Tyr Thr Phe Thr Asp Tyr
            20                  25                  30 gct atg cac tgg gtg aag cag agt cct ggc aag agt ctg gag tgg att     144
Ala Met His Trp Val Lys Gln Ser Pro Gly Lys Ser Leu Glu Trp Ile
        35                  40                  45 gga gtt att agt act aag tat ggt aag aca aac tac aac ccc agc ttt     192
Gly Val Ile Ser Thr Lys Tyr Gly Lys Thr Asn Tyr Asn Pro Ser Phe
    50                  55                  60 cag ggc cag gcc aca atg act gtt gac aaa tcc tcc agc aca gcc tat     240
Gln Gly Gln Ala Thr Met Thr Val Asp Lys Ser Ser Ser Thr Ala Tyr
65                  70                  75                  80 atg gag ctt gcc agc ttg aag gcc tcc gat tct gcc atc tat tac tgt     288
Met Glu Leu Ala Ser Leu Lys Ala Ser Asp Ser Ala Ile Tyr Tyr Cys
```

-continued

|  |  |  |  |  |  |  |  |  |  |  |  |  |  |  |  |
|---|---|---|---|---|---|---|---|---|---|---|---|---|---|---|---|
|  |  | 85 |  |  |  | 90 |  |  |  |  | 95 |  |  |  |  |
| gca | aga | ggg | gac | gat | ggt | tat | tcc | tgg | ggt | caa | gga | acc | tca | gtc | acc | 336 |
| Ala | Arg | Gly | Asp | Asp | Gly | Tyr | Ser | Trp | Gly | Gln | Gly | Thr | Ser | Val | Thr |
|  |  | 100 |  |  |  | 105 |  |  |  |  | 110 |  |  |  |  |
| gtc | tcc | agc | gct | tct | acc | aag | ggc | cct | tcc | gtg | ttc | cct | ctg | gcc | cct | 384 |
| Val | Ser | Ser | Ala | Ser | Thr | Lys | Gly | Pro | Ser | Val | Phe | Pro | Leu | Ala | Pro |
|  |  | 115 |  |  |  | 120 |  |  |  |  | 125 |  |  |  |  |
| tgc | tcc | cgg | tcc | acc | tcc | gag | tcc | acc | gcc | gct | ctg | ggc | tgc | ctg | gtg | 432 |
| Cys | Ser | Arg | Ser | Thr | Ser | Glu | Ser | Thr | Ala | Ala | Leu | Gly | Cys | Leu | Val |
|  |  | 130 |  |  |  | 135 |  |  |  |  | 140 |  |  |  |  |
| aag | gac | tac | ttc | cct | gag | cct | gtg | acc | gtg | tcc | tgg | aac | tct | ggc | gcc | 480 |
| Lys | Asp | Tyr | Phe | Pro | Glu | Pro | Val | Thr | Val | Ser | Trp | Asn | Ser | Gly | Ala |
| 145 |  |  |  |  | 150 |  |  |  |  | 155 |  |  |  |  | 160 |
| ctg | acc | tcc | ggc | gtg | cac | acc | ttc | cct | gcc | gtg | ctg | cag | tcc | tcc | ggc | 528 |
| Leu | Thr | Ser | Gly | Val | His | Thr | Phe | Pro | Ala | Val | Leu | Gln | Ser | Ser | Gly |
|  |  |  |  | 165 |  |  |  |  | 170 |  |  |  |  | 175 |  |
| ctg | tac | tcc | ctg | tcc | tcc | gtg | gtg | acc | gtg | cct | tcc | tcc | tcc | ctg | ggc | 576 |
| Leu | Tyr | Ser | Leu | Ser | Ser | Val | Val | Thr | Val | Pro | Ser | Ser | Ser | Leu | Gly |
|  |  |  | 180 |  |  |  |  | 185 |  |  |  |  | 190 |  |  |
| acc | aag | acc | tac | acc | tgt | aac | gtg | gac | cac | aag | cct | tcc | aac | acc | aag | 624 |
| Thr | Lys | Thr | Tyr | Thr | Cys | Asn | Val | Asp | His | Lys | Pro | Ser | Asn | Thr | Lys |
|  |  | 195 |  |  |  | 200 |  |  |  |  | 205 |  |  |  |  |
| gtg | gac | aag | cgg | gtg | gag | tcc | aag | tac | ggc | cct | cct | tgc | cct | ccc | tgc | 672 |
| Val | Asp | Lys | Arg | Val | Glu | Ser | Lys | Tyr | Gly | Pro | Pro | Cys | Pro | Pro | Cys |
|  |  | 210 |  |  |  | 215 |  |  |  |  | 220 |  |  |  |  |
| cct | gcc | cct | gag | ttc | gag | ggc | gga | cct | agc | gtg | ttc | ctg | ttc | cct | cct | 720 |
| Pro | Ala | Pro | Glu | Phe | Glu | Gly | Gly | Pro | Ser | Val | Phe | Leu | Phe | Pro | Pro |
| 225 |  |  |  |  | 230 |  |  |  |  | 235 |  |  |  |  | 240 |
| aag | cct | aag | gac | acc | ctg | atg | atc | tcc | cgg | acc | cct | gag | gtg | acc | tgt | 768 |
| Lys | Pro | Lys | Asp | Thr | Leu | Met | Ile | Ser | Arg | Thr | Pro | Glu | Val | Thr | Cys |
|  |  |  |  | 245 |  |  |  |  | 250 |  |  |  |  | 255 |  |
| gtg | gtg | gtg | gac | gtg | tcc | cag | gag | gac | cct | gag | gtc | cag | ttc | aac | tgg | 816 |
| Val | Val | Val | Asp | Val | Ser | Gln | Glu | Asp | Pro | Glu | Val | Gln | Phe | Asn | Trp |
|  |  |  | 260 |  |  |  |  | 265 |  |  |  |  | 270 |  |  |
| tac | gtg | gac | ggc | gtg | gag | gtg | cac | aac | gcc | aag | acc | aag | cct | cgg | gag | 864 |
| Tyr | Val | Asp | Gly | Val | Glu | Val | His | Asn | Ala | Lys | Thr | Lys | Pro | Arg | Glu |
|  |  | 275 |  |  |  | 280 |  |  |  |  | 285 |  |  |  |  |
| gag | cag | ttc | aat | tcc | acc | tac | cgg | gtg | gtg | tct | gtg | ctg | acc | gtg | ctg | 912 |
| Glu | Gln | Phe | Asn | Ser | Thr | Tyr | Arg | Val | Val | Ser | Val | Leu | Thr | Val | Leu |
|  |  | 290 |  |  |  | 295 |  |  |  |  | 300 |  |  |  |  |
| cac | cag | gac | tgg | ctg | aac | ggc | aaa | gaa | tac | aag | tgt | aag | gtc | tcc | aac | 960 |
| His | Gln | Asp | Trp | Leu | Asn | Gly | Lys | Glu | Tyr | Lys | Cys | Lys | Val | Ser | Asn |
| 305 |  |  |  |  | 310 |  |  |  |  | 315 |  |  |  |  | 320 |
| aag | ggc | ctg | ccc | tcc | tcc | atc | gag | aaa | acc | atc | tcc | aag | gcc | aag | ggc | 1008 |
| Lys | Gly | Leu | Pro | Ser | Ser | Ile | Glu | Lys | Thr | Ile | Ser | Lys | Ala | Lys | Gly |
|  |  |  |  | 325 |  |  |  |  | 330 |  |  |  |  | 335 |  |
| cag | cct | agg | gag | cct | cag | gtg | tac | acc | ctg | cct | cct | agc | cag | gaa | gag | 1056 |
| Gln | Pro | Arg | Glu | Pro | Gln | Val | Tyr | Thr | Leu | Pro | Pro | Ser | Gln | Glu | Glu |
|  |  | 340 |  |  |  | 345 |  |  |  |  | 350 |  |  |  |  |
| atg | acc | aag | aac | cag | gtg | tcc | ctg | acc | tgt | ctg | gtg | aag | ggc | ttc | tac | 1104 |
| Met | Thr | Lys | Asn | Gln | Val | Ser | Leu | Thr | Cys | Leu | Val | Lys | Gly | Phe | Tyr |
|  |  | 355 |  |  |  | 360 |  |  |  |  | 365 |  |  |  |  |
| cct | tcc | gac | atc | gcc | gtg | gag | tgg | gag | tcc | aac | ggc | cag | cct | gag | aac | 1152 |
| Pro | Ser | Asp | Ile | Ala | Val | Glu | Trp | Glu | Ser | Asn | Gly | Gln | Pro | Glu | Asn |
|  |  | 370 |  |  |  | 375 |  |  |  |  | 380 |  |  |  |  |
| aac | tac | aag | acc | acc | cct | cct | gtg | ctg | gac | tcc | gac | ggc | tcc | ttc | ttc | 1200 |
| Asn | Tyr | Lys | Thr | Thr | Pro | Pro | Val | Leu | Asp | Ser | Asp | Gly | Ser | Phe | Phe |
| 385 |  |  |  |  | 390 |  |  |  |  | 395 |  |  |  |  | 400 |
| ctg | tac | tcc | agg | ctg | acc | gtg | gac | aag | tcc | cgg | tgg | cag | gag | ggc | aac | 1248 |

```
Leu Tyr Ser Arg Leu Thr Val Asp Lys Ser Arg Trp Gln Glu Gly Asn
                405                 410                 415
```

```
gtc ttt tcc tgc tcc gtg atg cac gag gcc ctg cac aac cac tac acc    1296
Val Phe Ser Cys Ser Val Met His Glu Ala Leu His Asn His Tyr Thr
            420                 425                 430
```

```
cag aag tcc ctg tcc ctg tct ctg ggc tga                            1326
Gln Lys Ser Leu Ser Leu Ser Leu Gly
        435                 440
```

<210> SEQ ID NO 2
<211> LENGTH: 441
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Leu Gln Gln Ser Gly Pro Glu Val Val Lys Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser Pro Gly Lys Ser Leu Glu Trp Ile
        35                  40                  45

Gly Val Ile Ser Thr Lys Tyr Gly Lys Thr Asn Tyr Asn Pro Ser Phe
    50                  55                  60

Gln Gly Gln Ala Thr Met Thr Val Asp Lys Ser Ser Thr Ala Tyr
65                  70                  75                  80

Met Glu Leu Ala Ser Leu Lys Ala Ser Asp Ser Ala Ile Tyr Tyr Cys
                85                  90                  95

Ala Arg Gly Asp Asp Gly Tyr Ser Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
```

```
                305                 310                 315                 320
Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
                340                 345                 350

Met Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
                420                 425                 430

Gln Lys Ser Leu Ser Leu Ser Leu Gly
                435                 440

<210> SEQ ID NO 3
<211> LENGTH: 660
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(660)

<400> SEQUENCE: 3 gag atc gtg atg acc caa act cca ctc tcc ctg cct gtc agt ctt gga       48
Glu Ile Val Met Thr Gln Thr Pro Leu Ser Leu Pro Val Ser Leu Gly
1               5                   10                  15 gat aga gcc tcc atc tct tgc aga tct ggt cag agc ctt gtg cac agt       96
Asp Arg Ala Ser Ile Ser Cys Arg Ser Gly Gln Ser Leu Val His Ser
            20                  25                  30 aat gga aac acc tat ctg cat tgg tac ctg cag aag cca ggc cag tct      144
Asn Gly Asn Thr Tyr Leu His Trp Tyr Leu Gln Lys Pro Gly Gln Ser
        35                  40                  45 cca aag ctc ctg atc tat aca gtt tcc aac cga ttt tct ggg gtc ccg      192
Pro Lys Leu Leu Ile Tyr Thr Val Ser Asn Arg Phe Ser Gly Val Pro
    50                  55                  60 gac agg ttc agt ggc agt gga tca ggg tca gat ttc aca ctc acc atc      240
Asp Arg Phe Ser Gly Ser Gly Ser Gly Ser Asp Phe Thr Leu Thr Ile
65                  70                  75                  80 agc aga gtg gag gct gag gat ctg gga gtt tat ttc tgc tct caa aat      288
Ser Arg Val Glu Ala Glu Asp Leu Gly Val Tyr Phe Cys Ser Gln Asn
                85                  90                  95 aca ttt gtt cct tgg acg ttc ggt gga ggc acc aag ctg gaa atc aaa      336
Thr Phe Val Pro Trp Thr Phe Gly Gly Gly Thr Lys Leu Glu Ile Lys
            100                 105                 110 cgt acg gtg gct gca cca tct gtc ttc atc ttc ccg cca tct gat gag      384
Arg Thr Val Ala Ala Pro Ser Val Phe Ile Phe Pro Pro Ser Asp Glu
        115                 120                 125 cag ttg aaa tct gga act gcc tct gtt gtg tgc ctg ctg aat aac ttc      432
Gln Leu Lys Ser Gly Thr Ala Ser Val Val Cys Leu Leu Asn Asn Phe
    130                 135                 140 tat ccc aga gag gcc aaa gta cag tgg aag gtg gat aac gcc ctc caa      480
Tyr Pro Arg Glu Ala Lys Val Gln Trp Lys Val Asp Asn Ala Leu Gln
145                 150                 155                 160
```

```
tcg ggt aac tcc cag gag agt gtc aca gag cag gac agc aag gac agc      528
Ser Gly Asn Ser Gln Glu Ser Val Thr Glu Gln Asp Ser Lys Asp Ser
            165                 170                 175 acc tac agc ctc agc agc acc ctg acg ctg agc aaa gca gac tac gag      576
Thr Tyr Ser Leu Ser Ser Thr Leu Thr Leu Ser Lys Ala Asp Tyr Glu
        180                 185                 190 aaa cac aaa gtc tac gcc tgc gaa gtc acc cat cag ggc ctg agc tcg      624
Lys His Lys Val Tyr Ala Cys Glu Val Thr His Gln Gly Leu Ser Ser
    195                 200                 205 ccc gtc aca aag agc ttc aac agg gga gag tgt tga                      660
Pro Val Thr Lys Ser Phe Asn Arg Gly Glu Cys
    210                 215
```

<210> SEQ ID NO 4
<211> LENGTH: 219
<212> TYPE: PRT
<213> ORGANISM: Artificial Sequence
<220> FEATURE:
<223> OTHER INFORMATION: Synthetic Construct

<400> SEQUENCE: 4

```
Glu Ile Val Met Thr Gln Thr Pro Leu Ser Leu Pro Val Ser Leu Gly
1               5                   10                  15

Asp Arg Ala Ser Ile Ser Cys Arg Ser Gly Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Ser Asp Phe Thr Leu Thr Ile
65                  70                  75                  80

Ser Arg Val Glu Ala Glu Asp Leu Gly Val Tyr Phe Cys Ser Gln Asn
                85                  90                  95

Thr Phe Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 5
<211> LENGTH: 345
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(345)

<400> SEQUENCE: 5

| gag | gtc | cag | ctg | cag | cag | tct | ggg | cct | gag | gtg | gtg | aag | cct | ggg | gtc | 48 |
|---|---|---|---|---|---|---|---|---|---|---|---|---|---|---|---|---|
| Glu | Val | Gln | Leu | Gln | Gln | Ser | Gly | Pro | Glu | Val | Val | Lys | Pro | Gly | Val | |
| 1 | | | | 5 | | | | | 10 | | | | | 15 | | |

| tca | gtg | aag | att | tcc | tgc | aag | ggt | tcc | ggc | tac | aca | ttc | act | gat | tat | 96 |
|---|---|---|---|---|---|---|---|---|---|---|---|---|---|---|---|---|
| Ser | Val | Lys | Ile | Ser | Cys | Lys | Gly | Ser | Gly | Tyr | Thr | Phe | Thr | Asp | Tyr | |
| | | | 20 | | | | | 25 | | | | | 30 | | | |

| gct | atg | cac | tgg | gtg | aag | cag | agt | cct | ggc | aag | agt | ctg | gag | tgg | att | 144 |
|---|---|---|---|---|---|---|---|---|---|---|---|---|---|---|---|---|
| Ala | Met | His | Trp | Val | Lys | Gln | Ser | Pro | Gly | Lys | Ser | Leu | Glu | Trp | Ile | |
| | | 35 | | | | | 40 | | | | | 45 | | | | |

| gga | gtt | att | agt | act | aag | tat | ggt | aag | aca | aac | tac | aac | ccc | agc | ttt | 192 |
|---|---|---|---|---|---|---|---|---|---|---|---|---|---|---|---|---|
| Gly | Val | Ile | Ser | Thr | Lys | Tyr | Gly | Lys | Thr | Asn | Tyr | Asn | Pro | Ser | Phe | |
| 50 | | | | | 55 | | | | | 60 | | | | | | |

| cag | ggc | cag | gcc | aca | atg | act | gtt | gac | aaa | tcc | tcc | agc | aca | gcc | tat | 240 |
|---|---|---|---|---|---|---|---|---|---|---|---|---|---|---|---|---|
| Gln | Gly | Gln | Ala | Thr | Met | Thr | Val | Asp | Lys | Ser | Ser | Ser | Thr | Ala | Tyr | |
| 65 | | | | 70 | | | | | 75 | | | | | 80 | | |

| atg | gag | ctt | gcc | agc | ttg | aag | gcc | tcc | gat | tct | gcc | atc | tat | tac | tgt | 288 |
|---|---|---|---|---|---|---|---|---|---|---|---|---|---|---|---|---|
| Met | Glu | Leu | Ala | Ser | Leu | Lys | Ala | Ser | Asp | Ser | Ala | Ile | Tyr | Tyr | Cys | |
| | | | | 85 | | | | | 90 | | | | | 95 | | |

| gca | aga | ggg | gac | gat | ggt | tat | tcc | tgg | ggt | caa | gga | acc | tca | gtc | acc | 336 |
|---|---|---|---|---|---|---|---|---|---|---|---|---|---|---|---|---|
| Ala | Arg | Gly | Asp | Asp | Gly | Tyr | Ser | Trp | Gly | Gln | Gly | Thr | Ser | Val | Thr | |
| | | | 100 | | | | | 105 | | | | | 110 | | | |

| gtc | tcc | agc | 345 |
|---|---|---|---|
| Val | Ser | Ser | |
| | | 115 | |

<210> SEQ ID NO 6
<211> LENGTH: 115
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Gln Gln Ser Gly Pro Glu Val Val Lys Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser Pro Gly Lys Ser Leu Glu Trp Ile
        35                  40                  45

Gly Val Ile Ser Thr Lys Tyr Gly Lys Thr Asn Tyr Asn Pro Ser Phe
    50                  55                  60

Gln Gly Gln Ala Thr Met Thr Val Asp Lys Ser Ser Ser Thr Ala Tyr
65                  70                  75                  80

Met Glu Leu Ala Ser Leu Lys Ala Ser Asp Ser Ala Ile Tyr Tyr Cys
                85                  90                  95

Ala Arg Gly Asp Asp Gly Tyr Ser Trp Gly Gln Gly Thr Ser Val Thr
            100                 105                 110

Val Ser Ser
        115

<210> SEQ ID NO 7
<211> LENGTH: 339
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(339)

<400> SEQUENCE: 7

```
gag atc gtg atg acc caa act cca ctc tcc ctg cct gtc agt ctt gga      48
Glu Ile Val Met Thr Gln Thr Pro Leu Ser Leu Pro Val Ser Leu Gly
1               5                   10                  15 gat aga gcc tcc atc tct tgc aga tct ggt cag agc ctt gtg cac agt      96
Asp Arg Ala Ser Ile Ser Cys Arg Ser Gly Gln Ser Leu Val His Ser
            20                  25                  30 aat gga aac acc tat ctg cat tgg tac ctg cag aag cca ggc cag tct     144
Asn Gly Asn Thr Tyr Leu His Trp Tyr Leu Gln Lys Pro Gly Gln Ser
        35                  40                  45 cca aag ctc ctg atc tat aca gtt tcc aac cga ttt tct ggg gtc ccg     192
Pro Lys Leu Leu Ile Tyr Thr Val Ser Asn Arg Phe Ser Gly Val Pro
    50                  55                  60 gac agg ttc agt ggc agt gga tca ggg tca gat ttc aca ctc acc atc     240
Asp Arg Phe Ser Gly Ser Gly Ser Gly Ser Asp Phe Thr Leu Thr Ile
65                  70                  75                  80 agc aga gtg gag gct gag gat ctg gga gtt tat ttc tgc tct caa aat     288
Ser Arg Val Glu Ala Glu Asp Leu Gly Val Tyr Phe Cys Ser Gln Asn
                85                  90                  95 aca ttt gtt cct tgg acg ttc ggt gga ggc acc aag ctg gaa atc aaa     336
Thr Phe Val Pro Trp Thr Phe Gly Gly Gly Thr Lys Leu Glu Ile Lys
            100                 105                 110 cgt                                                                 339
Arg
```

<210> SEQ ID NO 8
<211> LENGTH: 113
<212> TYPE: PRT
<213> ORGANISM: Artificial Sequence
<220> FEATURE:
<223> OTHER INFORMATION: Synthetic Construct

<400> SEQUENCE: 8

```
Glu Ile Val Met Thr Gln Thr Pro Leu Ser Leu Pro Val Ser Leu Gly
1               5                   10                  15

Asp Arg Ala Ser Ile Ser Cys Arg Ser Gly Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Ser Asp Phe Thr Leu Thr Ile
65                  70                  75                  80

Ser Arg Val Glu Ala Glu Asp Leu Gly Val Tyr Phe Cys Ser Gln Asn
                85                  90                  95

Thr Phe Val Pro Trp Thr Phe Gly Gly Gly Thr Lys Leu Glu Ile Lys
            100                 105                 110

Arg
```

<210> SEQ ID NO 9
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 9

```
tcc ggc tac aca ttc act gat tat gct atg cac                          33
Ser Gly Tyr Thr Phe Thr Asp Tyr Ala Met His
```

```
<210> SEQ ID NO 10
<211> LENGTH: 11
<212> TYPE: PRT
<213> ORGANISM: Mus musculus

<400> SEQUENCE: 10

Ser Gly Tyr Thr Phe Thr Asp Tyr Ala Met His
1               5                   10

<210> SEQ ID NO 11
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 11 gtt att agt act aag tat ggt aag aca aac                           30
Val Ile Ser Thr Lys Tyr Gly Lys Thr Asn
1               5                   10

<210> SEQ ID NO 12
<211> LENGTH: 10
<212> TYPE: PRT
<213> ORGANISM: Mus musculus

<400> SEQUENCE: 12

Val Ile Ser Thr Lys Tyr Gly Lys Thr Asn
1               5                   10

<210> SEQ ID NO 13
<211> LENGTH: 18
<212> TYPE: DNA
<213> ORGANISM: Mus musculus
<220> FEATURE:
<221> NAME/KEY: CDS
<222> LOCATION: (1)..(18)

<400> SEQUENCE: 13 ggg gac gat ggt tat tcc                                           18
Gly Asp Asp Gly Tyr Ser
1               5

<210> SEQ ID NO 14
<211> LENGTH: 6
<212> TYPE: PRT
<213> ORGANISM: Mus musculus

<400> SEQUENCE: 14

Gly Asp Asp Gly Tyr Ser
1               5

<210> SEQ ID NO 15
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 15 aga tct ggt cag agc ctt gtg cac agt aat gga aac acc tat ctg cat   48
Arg Ser Gly Gln Ser Leu Val His Ser Asn Gly Asn Thr Tyr Leu His
1               5                   10                  15
```

<210> SEQ ID NO 16
<211> LENGTH: 16
<212> TYPE: PRT
<213> ORGANISM: Mus musculus

<400> SEQUENCE: 16

Arg Ser Gly Gln Ser Leu Val His Ser Asn Gly Asn Thr Tyr Leu His
1               5                   10                  15

<210> SEQ ID NO 17
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 17 aca gtt tcc aac cga ttt tct ggg                                    24
Thr Val Ser Asn Arg Phe Ser Gly
1               5

<210> SEQ ID NO 18
<211> LENGTH: 8
<212> TYPE: PRT
<213> ORGANISM: Mus musculus

<400> SEQUENCE: 18

Thr Val Ser Asn Arg Phe Ser Gly
1               5

<210> SEQ ID NO 19
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 19 tct caa aat aca ttt gtt cct tgg acg                                27
Ser Gln Asn Thr Phe Val Pro Trp Thr
1               5

<210> SEQ ID NO 20
<211> LENGTH: 9
<212> TYPE: PRT
<213> ORGANISM: Mus musculus

<400> SEQUENCE: 20

Ser Gln Asn Thr Phe Val Pro Trp Thr
1               5

<210> SEQ ID NO 21
<211> LENGTH: 660
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(660)

<400> SEQUENCE: 21 gag atc gtg atg acc caa act cca ctc tcc ctg cct gtc agt ctt gga    48
Glu Ile Val Met Thr Gln Thr Pro Leu Ser Leu Pro Val Ser Leu Gly
1               5                   10                  15

```
                1               5                     10                        15
     gat aga gcc tcc atc tct tgc aga tct ggt cag agc ctt gtg cac agt          96
     Asp Arg Ala Ser Ile Ser Cys Arg Ser Gly Gln Ser Leu Val His Ser
                     20                  25                  30 aat acc aac acc tat ctg cat tgg tac ctg cag aag cca ggc cag tct         144
     Asn Thr Asn Thr Tyr Leu His Trp Tyr Leu Gln Lys Pro Gly Gln Ser
                     35                  40                  45 cca aag ctc ctg atc tat aca gtt tcc aac cga ttt tct ggg gtc ccg         192
     Pro Lys Leu Leu Ile Tyr Thr Val Ser Asn Arg Phe Ser Gly Val Pro
              50                  55                  60 gac agg ttc agt ggc agt gga tca ggg tca gat ttc aca ctc acc atc         240
     Asp Arg Phe Ser Gly Ser Gly Ser Gly Ser Asp Phe Thr Leu Thr Ile
     65                  70                  75                  80 agc aga gtg gag gct gag gat ctg gga gtt tat ttc tgc tct caa aat         288
     Ser Arg Val Glu Ala Glu Asp Leu Gly Val Tyr Phe Cys Ser Gln Asn
                     85                  90                  95 aca ttt gtt cct tgg acg ttc ggt gga ggc acc aag ctg gaa atc aaa         336
     Thr Phe Val Pro Trp Thr Phe Gly Gly Gly Thr Lys Leu Glu Ile Lys
                    100                 105                 110 cgt acg gtg gct gca cca tct gtc ttc atc ttc ccg cca tct gat gag         384
     Arg Thr Val Ala Ala Pro Ser Val Phe Ile Phe Pro Pro Ser Asp Glu
                    115                 120                 125 cag ttg aaa tct gga act gcc tct gtt gtg tgc ctg ctg aat aac ttc         432
     Gln Leu Lys Ser Gly Thr Ala Ser Val Val Cys Leu Leu Asn Asn Phe
             130                 135                 140 tat ccc aga gag gcc aaa gta cag tgg aag gtg gat aac gcc ctc caa         480
     Tyr Pro Arg Glu Ala Lys Val Gln Trp Lys Val Asp Asn Ala Leu Gln
     145                 150                 155                 160 tcg ggt aac tcc cag gag agt gtc aca gag cag gac agc aag gac agc         528
     Ser Gly Asn Ser Gln Glu Ser Val Thr Glu Gln Asp Ser Lys Asp Ser
                    165                 170                 175 acc tac agc ctc agc agc acc ctg acg ctg agc aaa gca gac tac gag         576
     Thr Tyr Ser Leu Ser Ser Thr Leu Thr Leu Ser Lys Ala Asp Tyr Glu
                    180                 185                 190 aaa cac aaa gtc tac gcc tgc gaa gtc acc cat cag ggc ctg agc tcg         624
     Lys His Lys Val Tyr Ala Cys Glu Val Thr His Gln Gly Leu Ser Ser
                    195                 200                 205 ccc gtc aca aag agc ttc aac agg gga gag tgt tga                         660
     Pro Val Thr Lys Ser Phe Asn Arg Gly Glu Cys
             210                 215

<210> SEQ ID NO 22
<211> LENGTH: 219
<212> TYPE: PRT
<213> ORGANISM: Artificial Sequence
<220> FEATURE:
<223> OTHER INFORMATION: Synthetic Construct

<400> SEQUENCE: 22

Glu Ile Val Met Thr Gln Thr Pro Leu Ser Leu Pro Val Ser Leu Gly
1               5                   10                  15

Asp Arg Ala Ser Ile Ser Cys Arg Ser Gly Gln Ser Leu Val His Ser
                20                  25                  30

Asn Thr Asn Thr Tyr Leu His Trp Tyr Leu Gln Lys Pro Gly Gln Ser
            35                  40                  45

Pro Lys Leu Leu Ile Tyr Thr Val Ser Asn Arg Phe Ser Gly Val Pro
        50                  55                  60

Asp Arg Phe Ser Gly Ser Gly Ser Gly Ser Asp Phe Thr Leu Thr Ile
65                  70                  75                  80
```

Ser Arg Val Glu Ala Glu Asp Leu Gly Val Tyr Phe Cys Ser Gln Asn
                85                  90                  95

Thr Phe Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 23
<211> LENGTH: 339
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(339)

<400> SEQUENCE: 23 gag atc gtg atg acc caa act cca ctc tcc ctg cct gtc agt ctt gga     48
Glu Ile Val Met Thr Gln Thr Pro Leu Ser Leu Pro Val Ser Leu Gly
1               5                   10                  15 gat aga gcc tcc atc tct tgc aga tct ggt cag agc ctt gtg cac agt     96
Asp Arg Ala Ser Ile Ser Cys Arg Ser Gly Gln Ser Leu Val His Ser
            20                  25                  30 aat acc aac acc tat ctg cat tgg tac ctg cag aag cca ggc cag tct    144
Asn Thr Asn Thr Tyr Leu His Trp Tyr Leu Gln Lys Pro Gly Gln Ser
        35                  40                  45 cca aag ctc ctg atc tat aca gtt tcc aac cga ttt tct ggg gtc ccg    192
Pro Lys Leu Leu Ile Tyr Thr Val Ser Asn Arg Phe Ser Gly Val Pro
    50                  55                  60 gac agg ttc agt ggc agt gga tca ggg tca gat ttc aca ctc acc atc    240
Asp Arg Phe Ser Gly Ser Gly Ser Gly Ser Asp Phe Thr Leu Thr Ile
65                  70                  75                  80 agc aga gtg gag gct gag gat ctg gga gtt tat ttc tgc tct caa aat    288
Ser Arg Val Glu Ala Glu Asp Leu Gly Val Tyr Phe Cys Ser Gln Asn
                85                  90                  95 aca ttt gtt cct tgg acg ttc ggt gga ggc acc aag ctg gaa atc aaa    336
Thr Phe Val Pro Trp Thr Phe Gly Gly Gly Thr Lys Leu Glu Ile Lys
            100                 105                 110 cgt                                                                339
Arg

<210> SEQ ID NO 24
<211> LENGTH: 113
<212> TYPE: PRT
<213> ORGANISM: Artificial Sequence
<220> FEATURE:
<223> OTHER INFORMATION: Synthetic Construct

<400> SEQUENCE: 24

```
Glu Ile Val Met Thr Gln Thr Pro Leu Ser Leu Pro Val Ser Leu Gly
1               5                   10                  15

Asp Arg Ala Ser Ile Ser Cys Arg Ser Gly Gln Ser Leu Val His Ser
            20                  25                  30

Asn Thr Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Asp Phe Thr Leu Thr Ile
65                  70                  75                  80

Ser Arg Val Glu Ala Glu Asp Leu Gly Val Tyr Phe Cys Ser Gln Asn
                85                  90                  95

Thr Phe Val Pro Trp Thr Phe Gly Gly Gly Thr Lys Leu Glu Ile Lys
            100                 105                 110

Arg
```

<210> SEQ ID NO 25
<211> LENGTH: 1326
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(1326)

<400> SEQUENCE: 25

```
gag gtc cag ctg cag cag tct ggg cct gag gtg gtg aag cct ggg gtc      48
Glu Val Gln Leu Gln Gln Ser Gly Pro Glu Val Val Lys Pro Gly Val
1               5                   10                  15 tca gtg aag att tcc tgc aag ggt tcc ggc tac aca ttc act gat tat      96
Ser Val Lys Ile Ser Cys Lys Gly Ser Gly Tyr Thr Phe Thr Asp Tyr
            20                  25                  30 gct atg cac tgg gtg aag cag agt cct ggc aag agt ctg gag tgg att     144
Ala Met His Trp Val Lys Gln Ser Pro Gly Lys Ser Leu Glu Trp Ile
        35                  40                  45 gga gtt att agt act aag tat ggt aag aca aac tac aac ccc agc ttt     192
Gly Val Ile Ser Thr Lys Tyr Gly Lys Thr Asn Tyr Asn Pro Ser Phe
    50                  55                  60 cag ggc cag gcc aca atg act gtt gac aaa tcc tcc agc aca gcc tat     240
Gln Gly Gln Ala Thr Met Thr Val Asp Lys Ser Ser Ser Thr Ala Tyr
65                  70                  75                  80 atg gag ctt gcc agc ttg aag gcc tcc gat tct gcc atc tat tac tgt     288
Met Glu Leu Ala Ser Leu Lys Ala Ser Asp Ser Ala Ile Tyr Tyr Cys
                85                  90                  95 gca aga ggg gac gag ggt tat tcc tgg ggt caa gga acc tca gtc acc     336
Ala Arg Gly Asp Glu Gly Tyr Ser Trp Gly Gln Gly Thr Ser Val Thr
            100                 105                 110 gtc tcc agc gct tct acc aag ggc cct tcc gtg ttc cct ctg gcc cct     384
Val Ser Ser Ala Ser Thr Lys Gly Pro Ser Val Phe Pro Leu Ala Pro
        115                 120                 125 tgc tcc cgg tcc acc tcc gag tcc acc gcc gct ctg ggc tgc ctg gtg     432
Cys Ser Arg Ser Thr Ser Glu Ser Thr Ala Ala Leu Gly Cys Leu Val
    130                 135                 140 aag gac tac ttc cct gag cct gtg acc gtg tcc tgg aac tct ggc gcc     480
Lys Asp Tyr Phe Pro Glu Pro Val Thr Val Ser Trp Asn Ser Gly Ala
145                 150                 155                 160 ctg acc tcc ggc gtg cac acc ttc cct gcc gtg ctg cag tcc tcc ggc     528
```

```
Leu Thr Ser Gly Val His Thr Phe Pro Ala Val Leu Gln Ser Ser Gly
                165                 170                 175 ctg tac tcc ctg tcc tcc gtg gtg acc gtg cct tcc tcc ctg ggc        576
Leu Tyr Ser Leu Ser Ser Val Val Thr Val Pro Ser Ser Ser Leu Gly
            180                 185                 190 acc aag acc tac acc tgt aac gtg gac cac aag cct tcc aac acc aag    624
Thr Lys Thr Tyr Thr Cys Asn Val Asp His Lys Pro Ser Asn Thr Lys
        195                 200                 205 gtg gac aag cgg gtg gag tcc aag tac ggc cct cct tgc cct ccc tgc    672
Val Asp Lys Arg Val Glu Ser Lys Tyr Gly Pro Pro Cys Pro Pro Cys
    210                 215                 220 cct gcc cct gag ttc gag ggc gga cct agc gtg ttc ctg ttc cct cct    720
Pro Ala Pro Glu Phe Glu Gly Gly Pro Ser Val Phe Leu Phe Pro Pro
225                 230                 235                 240 aag cct aag gac acc ctg atg atc tcc cgg acc cct gag gtg acc tgt    768
Lys Pro Lys Asp Thr Leu Met Ile Ser Arg Thr Pro Glu Val Thr Cys
                245                 250                 255 gtg gtg gtg gac gtg tcc cag gag gac cct gag gtc cag ttc aac tgg    816
Val Val Val Asp Val Ser Gln Glu Asp Pro Glu Val Gln Phe Asn Trp
            260                 265                 270 tac gtg gac ggc gtg gag gtg cac aac gcc aag acc aag cct cgg gag    864
Tyr Val Asp Gly Val Glu Val His Asn Ala Lys Thr Lys Pro Arg Glu
        275                 280                 285 gag cag ttc aat tcc acc tac cgg gtg gtg tct gtg ctg acc gtg ctg    912
Glu Gln Phe Asn Ser Thr Tyr Arg Val Val Ser Val Leu Thr Val Leu
    290                 295                 300 cac cag gac tgg ctg aac ggc aaa gaa tac aag tgt aag gtc tcc aac    960
His Gln Asp Trp Leu Asn Gly Lys Glu Tyr Lys Cys Lys Val Ser Asn
305                 310                 315                 320 aag ggc ctg ccc tcc tcc atc gag aaa acc atc tcc aag gcc aag ggc    1008
Lys Gly Leu Pro Ser Ser Ile Glu Lys Thr Ile Ser Lys Ala Lys Gly
                325                 330                 335 cag cct agg gag cct cag gtg tac acc ctg cct cct agc cag gaa gag    1056
Gln Pro Arg Glu Pro Gln Val Tyr Thr Leu Pro Pro Ser Gln Glu Glu
            340                 345                 350 atg acc aag aac cag gtg tcc ctg acc tgt ctg gtg aag ggc ttc tac    1104
Met Thr Lys Asn Gln Val Ser Leu Thr Cys Leu Val Lys Gly Phe Tyr
        355                 360                 365 cct tcc gac atc gcc gtg gag tgg gag tcc aac ggc cag cct gag aac    1152
Pro Ser Asp Ile Ala Val Glu Trp Glu Ser Asn Gly Gln Pro Glu Asn
    370                 375                 380 aac tac aag acc acc cct cct gtg ctg gac tcc gac ggc tcc ttc ttc    1200
Asn Tyr Lys Thr Thr Pro Pro Val Leu Asp Ser Asp Gly Ser Phe Phe
385                 390                 395                 400 ctg tac tcc agg ctg acc gtg gac aag tcc cgg tgg cag gag ggc aac    1248
Leu Tyr Ser Arg Leu Thr Val Asp Lys Ser Arg Trp Gln Glu Gly Asn
                405                 410                 415 gtc ttt tcc tgc tcc gtg atg cac gag gcc ctg cac aac cac tac acc    1296
Val Phe Ser Cys Ser Val Met His Glu Ala Leu His Asn His Tyr Thr
            420                 425                 430 cag aag tcc ctg tcc ctg tct ctg ggc tga                            1326
Gln Lys Ser Leu Ser Leu Ser Leu Gly
        435                 440

<210> SEQ ID NO 26
<211> LENGTH: 441
<212> TYPE: PRT
<213> ORGANISM: Artificial Sequence
<220> FEATURE:
<223> OTHER INFORMATION: Synthetic Construct
```

<400> SEQUENCE: 26

```
Glu Val Gln Leu Gln Gln Ser Gly Pro Glu Val Val Lys Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser Pro Gly Lys Ser Leu Glu Trp Ile
        35                  40                  45

Gly Val Ile Ser Thr Lys Tyr Gly Lys Thr Asn Tyr Asn Pro Ser Phe
    50                  55                  60

Gln Gly Gln Ala Thr Met Thr Val Asp Lys Ser Ser Thr Ala Tyr
65                  70                  75                  80

Met Glu Leu Ala Ser Leu Lys Ala Ser Asp Ser Ala Ile Tyr Tyr Cys
                85                  90                  95

Ala Arg Gly Asp Glu Gly Tyr Ser Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Glu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415
```

Val Phe Ser Cys Ser Val Met His Glu Ala Leu His Asn His Tyr Thr
            420                 425                 430
Gln Lys Ser Leu Ser Leu Ser Leu Gly
        435                 440

<210> SEQ ID NO 27
<211> LENGTH: 345
<212> TYPE: DNA
<213> ORGANISM: Artificial Sequence
<220> FEATURE:
<223> OTHER INFORMATION: Humanized sequence
<220> FEATURE:
<221> NAME/KEY: CDS
<222> LOCATION: (1)..(345)

<400> SEQUENCE: 27

```
gag gtc cag ctg cag cag tct ggg cct gag gtg gtg aag cct ggg gtc         48
Glu Val Gln Leu Gln Gln Ser Gly Pro Glu Val Val Lys Pro Gly Val
1               5                   10                  15 tca gtg aag att tcc tgc aag ggt tcc ggc tac aca ttc act gat tat         96
Ser Val Lys Ile Ser Cys Lys Gly Ser Gly Tyr Thr Phe Thr Asp Tyr
            20                  25                  30 gct atg cac tgg gtg aag cag agt cct ggc aag agt ctg gag tgg att       144
Ala Met His Trp Val Lys Gln Ser Pro Gly Lys Ser Leu Glu Trp Ile
        35                  40                  45 gga gtt att agt act aag tat ggt aag aca aac tac aac ccc agc ttt       192
Gly Val Ile Ser Thr Lys Tyr Gly Lys Thr Asn Tyr Asn Pro Ser Phe
    50                  55                  60 cag ggc cag gcc aca atg act gtt gac aaa tcc tcc agc aca gcc tat       240
Gln Gly Gln Ala Thr Met Thr Val Asp Lys Ser Ser Ser Thr Ala Tyr
65                  70                  75                  80 atg gag ctt gcc agc ttg aag gcc tct gat tct gcc atc tat tac tgt       288
Met Glu Leu Ala Ser Leu Lys Ala Ser Asp Ser Ala Ile Tyr Tyr Cys
                85                  90                  95 gca aga ggg gac gag ggt tat tcc tgg ggt caa gga acc tca gtc acc       336
Ala Arg Gly Asp Glu Gly Tyr Ser Trp Gly Gln Gly Thr Ser Val Thr
            100                 105                 110 gtc tcc agc                                                             345
Val Ser Ser
        115
```

<210> SEQ ID NO 28
<211> LENGTH: 115
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Gln Gln Ser Gly Pro Glu Val Val Lys Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser Pro Gly Lys Ser Leu Glu Trp Ile
        35                  40                  45

Gly Val Ile Ser Thr Lys Tyr Gly Lys Thr Asn Tyr Asn Pro Ser Phe
    50                  55                  60

Gln Gly Gln Ala Thr Met Thr Val Asp Lys Ser Ser Ser Thr Ala Tyr
65                  70                  75                  80

Met Glu Leu Ala Ser Leu Lys Ala Ser Asp Ser Ala Ile Tyr Tyr Cys
                85                  90                  95

```
Ala Arg Gly Asp Glu Gly Tyr Ser Trp Gly Gln Gly Thr Ser Val Thr
            100                 105                 110
Val Ser Ser
        115

<210> SEQ ID NO 29
<211> LENGTH: 18
<212> TYPE: DNA
<213> ORGANISM: Mus musculus
<220> FEATURE:
<221> NAME/KEY: CDS
<222> LOCATION: (1)..(18)

<400> SEQUENCE: 29 ggg gac gag ggt tat tcc                                          18
Gly Asp Glu Gly Tyr Ser
1               5

<210> SEQ ID NO 30
<211> LENGTH: 6
<212> TYPE: PRT
<213> ORGANISM: Mus musculus

<400> SEQUENCE: 30

Gly Asp Glu Gly Tyr Ser
1               5

<210> SEQ ID NO 31
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 31 aga tct ggt cag agc ctt gtg cac agt aat acc aac acc tat ctg cat   48
Arg Ser Gly Gln Ser Leu Val His Ser Asn Thr Asn Thr Tyr Leu His
1               5                   10                  15

<210> SEQ ID NO 32
<211> LENGTH: 16
<212> TYPE: PRT
<213> ORGANISM: Mus musculus

<400> SEQUENCE: 32

Arg Ser Gly Gln Ser Leu Val His Ser Asn Thr Asn Thr Tyr Leu His
1               5                   10                  15
```

HUMANIZED ANTIBODIES SPECIFIC TO THE PROTOFIBRILLAR FORM OF THE BETA-AMYLOID PEPTIDE

RELATED APPLICATIONS

This application is division of U.S. application Ser. No. 13/319,710, filed on Mar. 26, 2012, now U.S. Pat. No. 8,614,299, which is a 35 U.S.C. §371 filing of International Application Number PCT/FR2010/050915, filed on May 11, 2010, the contents of each of which are incorporated by reference herein in their entirety.

The present invention relates to humanized antibodies specific for the protofibrillar form of β-amyloid peptide. The present invention also relates to the therapeutic, diagnostic and/or preventive use of these antibodies, in particular associated with the induction and with the progression of neurodegenerative disorders and/or with diseases associated with the deposition of amyloid plaques, and notably Alzheimer's disease.

Alzheimer's disease (AD) is a progressive neurodegenerative disease that affects a high proportion of the older population. This disease is characterized clinically by memory loss and a decline in cognitive functions, and neuropathologically by the presence, in the brain, of intracellular neurofibrillar deposits and of extracellular deposits of the β-amyloid peptide (A-β) forming amyloid plaques. (Yanker et al. Nature Med. Vol. 2 No. 8 (1996)). As well as these signs, there are many other abnormal changes including a deterioration of the immune and inflammatory systems as well as a deterioration of mitochondrial function, which can lead to an increase in oxidative stress, activation of the mechanisms of apoptosis and ultimately to cell death.

Amyloid plaques are predominantly composed of A-β peptides with 40 or 42 residues, which are generated during the proteolytic process of the β-amyloid peptide precursor (APP) protein. The extracellular deposits of A-β peptides represent the invariable early characteristic feature of all forms of AD, including the familial forms (FAD). FADs appear relatively early (between 40 and 60 years) and are due to mutations in the gene of APP in 5% of cases of FAD (>20 families) with six single or double missense mutations; in the gene of presenilin 1 (PS 1) in 50 to 70% of cases of FAD (>200 families) with more than 80 different mutations identified to date; and in the gene of presenilin 2 (PS 2) in fewer cases of FAD with 2 missense mutations described in 8 families. Mutations in these three genes have been shown to induce changes in the proteolysis of APP, which lead to overproduction of A-β and to the early appearance of the pathology and of symptoms that are similar to those of the sporadic forms of AD.

The neuronal toxicity of the amyloid plaques might reside in the high molecular weight fibrils that are formed by aggregation of soluble A-β peptides in fibrillar forms that are soluble initially (also called protofibrillar form) and are then converted to insoluble forms incorporated in the amyloid plaques. In fact, it was shown in vitro that the soluble A-β peptide aggregates progressively to a fibrillar form (i.e. which can be labelled with agents such as Congo Red or thioflavin S which recognize the beta-sheet tertiary structures of the peptides/proteins), of high molecular weight (>200 kDa) but still soluble. Because this form is soluble, it is often called the protofibrillar form, whereas the fibrils result from even greater aggregation, leading to loss of solubility. The protofibrillar transitional forms are generally regarded as the precursors of the amyloid fibres and might be responsible for the cellular dysfunction and the neuronal loss in Alzheimer's disease and in other diseases associated with the aggregation of proteins.

It has been shown that the senile amyloid plaques (i.e. aggregated, also called mature plaques) are correlated with the cognitive status of Alzheimer's patients in contrast to the diffuse deposits of A-β peptide which are also widely present in unaffected patients. (Duyckaerts et al., Neurobiol. Aging 1997; 18: 33-42 and Jellinger et al., 1998; 54:77-95). By targeting these senile amyloid plaques in particular, it is therefore possible to treat Alzheimer's disease more specifically and effectively.

A great many treatments have been tried for preventing the formation of the A-β peptides, for example inhibitors of the proteolytic process of APP. Immunotherapeutic strategies such as the administration of anti-A-β antibody (to reduce the amyloid deposits) or immunization with antigens of the A-β peptides (to promote a humoral response) have been tested in order to reduce the size and density of the plaques.

For example, a method of treatment against Alzheimer's disease has been described (U.S. Pat. No. 7,179,463), consisting of administering an antibody directed against a protofibril presenting an Arctic mutation in the region coding for the A-β peptide.

No example of antibody has really been described. Moreover, no comparison of the affinity of the antibodies for the peptides as a function of the molecular weight of these peptides has been performed. Other patents (U.S. Pat. No. 6,761,888 and U.S. Pat. No. 6,750,324) have referred to antibodies recognizing various epitopes along the amino acid sequence of the peptide A-$\beta_{42}$. An international application (WO2007/108756) has been filed concerning antibodies specific for the protofibrils but the antibodies described recognize both the high molecular weight A-β peptides and the medium-weight oligomers. Furthermore, there is no mention of the affinity of the antibodies for the mature plaques relative to their affinity for the diffuse plaques.

Despite the current development of knowledge concerning Alzheimer's disease, there is still a need for compositions and methods of treatment and/or prevention of this pathology limiting the secondary effects to the maximum extent. Antibodies such as described in the present application, humanized and specific for the protofibrillar form of the A-β peptides, aim to solve this problem. Permitting recognition of the senile amyloid plaques but not the diffuse plaques, the antibodies according to the invention recognize the pathological plaques much more effectively than antibodies recognizing all forms of Abeta, which will largely be attached to the diffuse deposits or attached to the soluble forms of monomeric or low-molecular-weight A-β peptide.

Moreover, the fact that only the protofibrillar forms of the A-β peptides are recognized and not the protofibrillar forms of other proteins not linked to Alzheimer's disease avoids useless binding that may reduce the concentration of antibodies that are effective against the disease.

The murine antibody that has been humanized will be called antibody 13C3 throughout the present application.

The sequences that can code for or constitute the humanized antibodies according to the invention are shown in Table 2.

The present invention relates to a humanized antibody that binds specifically to the protofibrillar form of the A-β peptide, i.e. a high molecular weight peptide. In a more advantageous embodiment, the antibody binds to the A-β peptide having a molecular weight greater than 200, 300, 400 or 500 kDa.

According to one embodiment, the antibody according to the invention binds to the A-β peptides aggregated into senile plaques and not to the diffuse deposits of A-β peptides.

In an advantageous embodiment, the antibody according to the invention binds specifically to the protofibrillar form of the A-β peptide but not to the other proteins of amyloid structure (for example IAPP, Islet Amyloid Polypeptide).

The present invention also relates to a humanized antibody having reduced effector functions, making it possible to limit adverse effects such as the development of microhaemorrhages and vasogenic oedemas.

In an advantageous embodiment, the antibody according to the invention no longer possesses effector functions.

In an even more advantageous embodiment, the antibody is an immunoglobulin G 4 whose Fc domain has undergone mutations reducing the production of half-molecules.

In an even more advantageous embodiment, the antibody is an immunoglobulin G 4 whose Fc domain has undergone mutations reducing the effector activity.

The present invention relates to a humanized antibody comprising at least one CDR encoded by a nucleotide sequence having a sequence identical to one of the sequences SEQ ID NO: 9, 11, 13, 15, 17 and 19, or by sequences differing respectively by 1, 2, 3, 4 or 5 nucleotides from these sequences.

The present invention also relates to a humanized antibody comprising at least one CDR having a sequence identical to one of the sequences SEQ ID NO: 10, 12, 14, 16, 18 and 20.

In another embodiment, the antibody according to the invention comprises at least one CDR whose sequence differs by one to two amino acids relative to one of the sequences SEQ ID NO: 10, 12, 14, 16, 18, 20 and 32, inasmuch as the antibody maintains its binding specificity.

In an advantageous embodiment, the antibody comprises the CDRs encoded by the nucleotide sequences SEQ ID NO: 9, 11, 13, 15, 17 and 19, or by sequences differing respectively by 1, 2, 3, 4 or 5 nucleotides from these sequences.

In another advantageous embodiment, the antibody comprises the CDRs of sequence SEQ ID NO: 10, 12, 14, 16, 18 and 20.

The antibody according to the invention can also comprise the CDRs encoded by the nucleotide sequences SEQ ID NO: 9, 11, 13, 31, 17 and 19 or by sequences differing respectively by 1, 2, 3, 4 or 5 nucleotides from these sequences.

In an advantageous embodiment, the antibody according to the invention comprises the CDRs of sequence SEQ ID NO: 10, 12, 14, 32, 18 and 20.

One object of the invention is the humanized antibody comprising the CDRs encoded by the nucleotide sequences SEQ ID NO: 9, 11, 29, 31, 17 and 19 or by sequences differing respectively by 1, 2, 3, 4 or 5 nucleotides from these sequences. The invention also relates to a humanized antibody comprising the CDRs of sequence SEQ ID NO: 10, 12, 30, 32, 18 and 20.

In an advantageous embodiment, the antibody according to the invention comprises a variable part of its heavy chain (VH) encoded by a sequence having at least 80%, 85%, 90%, 95% or 99% identity with the sequence SEQ ID NO: 5 or the sequence SEQ ID NO 27.

In an advantageous embodiment, the antibody according to the invention comprises a variable part of its heavy chain (VH) comprising a sequence having at least 80%, 85%, 90%, 95% or 99% identity with the sequence SEQ ID NO: 6 or the sequence SEQ ID NO 28.

In an advantageous embodiment, the antibody according to the invention comprises a variable part of its light chain (VL) encoded by a sequence having at least 80%, 85%, 90%, 95% or 99% identity with the sequence SEQ ID NO: 7 or the sequence SEQ ID NO 23.

In an advantageous embodiment, the antibody according to the invention comprises a variable part of its light chain (VL) comprising a sequence having at least 80%, 85%, 90%, 95% or 99% identity with the sequence SEQ ID NO: 8 or the sequence SEQ ID NO 24.

In an even more advantageous embodiment, the antibody comprises a heavy chain comprising a variable part (VH) encoded by one of the nucleotide sequences SEQ ID NO 5 and SEQ ID NO 27.

In an even more advantageous embodiment, the antibody comprises a heavy chain comprising a variable part (VH) of polypeptide sequence SEQ ID NO 6 or SEQ ID NO 28.

In another embodiment, the antibody comprises a light chain comprising a variable part (VL) encoded by one of the nucleotide sequences SEQ ID NO 7 and SEQ ID NO 23.

In another embodiment, the antibody comprises a light chain comprising a variable part (VL) of polypeptide sequence SEQ ID NO 8 or SEQ ID NO 24.

In an advantageous embodiment, the antibody comprises the sequences encoded by the nucleotide sequences SEQ ID NO: 5 and 7.

In an advantageous embodiment, the antibody comprises the polypeptide sequences SEQ ID NO: 6 and 8.

In another embodiment, the antibody comprises the sequences encoded by the nucleotide sequences SEQ ID NO: 5 and 23.

In another embodiment, the antibody comprises the polypeptide sequences SEQ ID NO: 6 and 24.

In another embodiment, the antibody comprises the sequences encoded by the nucleotide sequences SEQ ID NO: 27 and 23.

In another embodiment, the antibody comprises the polypeptide sequences SEQ ID NO: 28 and 24.

The present invention also relates to an antibody comprising a heavy chain encoded by a sequence having at least 80%, 85%, 90%, 95% or 99% identity with one of the nucleotide sequences SEQ ID NO 1 and SEQ ID NO 25.

The present invention also relates to an antibody comprising a heavy chain having at least 80%, 85%, 90%, 95% or 99% identity with the polypeptide sequence SEQ ID NO 2 or with the polypeptide sequence SEQ ID NO 26.

In an advantageous embodiment the antibody comprises a light chain encoded by a sequence having at least 80%, 85%, 90%, 95% or 99% identity with one of the nucleotide sequences SEQ ID NO 3 and SEQ ID NO 21.

In another embodiment the antibody comprises a light chain comprising a sequence having at least 80%, 85%, 90%, 95% or 99% identity with one of the polypeptide sequences SEQ ID NO 4 and SEQ ID NO 22.

One object of the invention is an antibody comprising the sequences encoded by the nucleotide sequences SEQ ID NO: 1 and 3.

Another object of the invention is an antibody whose sequence comprises the polypeptide sequences SEQ ID NO: 2 and 4.

One object of the invention is an antibody comprising the sequences encoded by the nucleotide sequences SEQ ID NO: 1 and 21.

Another object of the invention is an antibody whose sequence comprises the polypeptide sequences SEQ ID NO: 2 and 22.

One object of the invention is an antibody comprising the sequences encoded by the nucleotide sequences SEQ ID NO: 25 and 21.

Another object of the invention is an antibody whose sequence comprises the polypeptide sequences SEQ ID NO: 26 and 22.

Another object of the invention is a humanized anti-peptide Aβ antibody having an affinity for the protofibrillar form of peptide Aβ at least 100 times greater than its affinity for the other forms of this peptide.

Another object of the invention is an antibody, characterized in that it induces a reduction of amyloid plaques.

Another object of the invention is the use of a humanized anti-peptide Aβ antibody in the treatment of diseases associated with neurodegenerative disorders, and in particular in the treatment of Alzheimer's disease.

Another object of the invention is a pharmaceutical composition comprising a humanized anti-peptide Aβ antibody and excipients.

Another object of the invention is a method of treatment of Alzheimer's disease comprising the administration of a humanized anti-peptide-Aβ antibody to the patient.

Another object of the invention is a cell or cells producing a humanized anti-peptide-Aβ antibody, as well as the method of production of this antibody comprising the culturing of these cells. Said cells are derived advantageously from one cell line.

One object of the invention is a medicinal product comprising a humanized anti-peptide-Aβ antibody.

One object of the invention is a polynucleotide coding for a polypeptide having at least 80%, 85%, 90%, 95% or 99% identity with one of the sequences SEQ ID NO: 2, 4, 6, 8, 22, 24, 26 or 28.

Another object of the invention is a polynucleotide with a sequence having at least 80%, 85%, 90%, 95% or 99% identity with one of the sequences SEQ ID NO: 1, 3, 5, 7, 21, 23, 25, or 27.

Another object of the invention is a recombinant vector comprising a nucleic acid having one of the sequences SEQ ID NO 1, 3, 5, 7, 21, 23, 25, or 27, as well as a host cell comprising this vector.

DEFINITIONS

Specific binding is understood as a difference by a factor of at least about 10, 20, 30, 40, 50, or 100 between the strength of binding to one receptor relative to another, here between binding to the protofibrillar form of the A-β peptide and binding to the other forms of the peptide.

"Epitope" means the site of the antigen to which the antibody binds. If the antigen is a polymer, such as a protein or a polysaccharide, the epitope can be formed by contiguous or non-contiguous residues. Here the epitope is conformational, i.e. related to the three-dimensional structure of the protofibrillar A-β peptide.

"Protofibrillar form" means an oligomeric form of A-β peptides, soluble in vitro and which can be isolated as an entity of molecular weight greater than 200 kDa, 300 kDa, 400 kDa or 500 kDa and which can fix agents such as thioflavin-S or Congo Red.

"Senile plaque" means a plaque composed of an amyloid core (fixing thioflavin S or Congo Red) surrounded by dystrophic neurites and a reaction of glial cells. Senile plaques are found in particular in patients with Alzheimer's disease, in contrast to the diffuse amyloid deposits (which do not fix thioflavin S or Congo Red), which are far more numerous but are not associated with the disease.

An antibody, also called immunoglobulin, is composed of two identical heavy chains ("CH") and two identical light chains ("CL"), which are joined by a disulphide bridge.

Each chain contains a constant region and a variable region. Each variable region comprises three segments called "complementarity determining regions" ("CDRs") or "hypervariable regions", which are mainly responsible for binding to the epitope of an antigen.

The term "VH" refers to the variable regions of a heavy chain of immunoglobulin of an antibody, including the heavy chains of a fragment Fv, scFv, dsFv, Fab, Fab' or F(ab)'.

The term "VL" refers to the variable regions of a light chain of immunoglobulin of an antibody, including the light chains of a fragment Fv, scFv, dsFv, Fab, Fab' or F(ab)'.

"Antibody" also means any functional fragment of antibody: Fab (Fragment antigen binding), Fv, scFv (single chain Fv), Fc (Fragment, crystallizable). Preferably, these functional fragments will be fragments of type Fv, scFv, Fab, F(ab') 2, Fab', scFv-Fc, diabodies, multispecific antibodies (notably bispecific), synthetic polypeptides containing the sequences of one or more CDRs, which generally possess the same specificity of fixation as the humanized antibody from which they are derived. According to the present invention, fragments of antibodies of the invention can be obtained from the humanized antibodies by methods such as digestion by enzymes, such as pepsin or papain and/or by cleavage of the disulphide bridges by chemical reduction.

Nanobodies also come under this definition.

"CDR or CDRs" denotes the hypervariable regions of the heavy and light chains of the immunoglobulins as defined by Kabat et al. (Kabat et al., Sequences of proteins of immunological interest, 5th Ed., U.S. Department of Health and Human Services, NIH, 1991, and later editions). There are 3 heavy-chain CDRs and 3 light-chain CDRs. The term CDR or CDRs is used here to denote, as applicable, one or more, or even all, of these regions that contain the majority of the amino acid residues responsible for the affine binding of the antibody for the antigen or the epitope that it recognizes. The most conserved regions of the variable domains are called FR regions or sequences, for "framework regions".

The present invention relates to humanized antibodies.

"Humanized antibody" means an antibody that contains mainly human immunoglobulin sequences. This term generally refers to a non-human immunoglobulin that has been modified by incorporating human sequences or residues found in human sequences.

In general, humanized antibodies comprise one or typically two variable domains in which all or part of the CDR regions correspond to parts derived from the non-human parent sequence and in which all or part of the FR regions are derived from a human immunoglobulin sequence. The humanized antibody can then comprise at least one portion of a constant region of immunoglobulin (Fc), in particular that of the selected reference human immunoglobulin.

We thus try to obtain an antibody that is the least immunogenic in a human. Thus it is possible that one or two amino acids of one or more CDRs are modified by an amino acid that is less immunogenic for the human host, without substantially reducing the binding specificity of the antibody to the A-β peptide of high molecular weight. Furthermore, the residues of the framework regions need not be human and it is possible that they are not modified, as they do not contribute to the immunogenic potential of the antibody.

Several methods of humanization are known by a person skilled in the art for modifying a non-human parent antibody to an antibody that is less immunogenic in humans. Complete identity of the sequences with a human antibody is not essential. In fact complete sequence identity is not necessarily a predictive indicator of reduced immunogenicity and modification of a limited number of residues can lead to humanized antibodies presenting a very attenuated immunogenic potential in humans (Molecular Immunology (2007) 44, 1986-1998).

Some methods are for example the inclusion of CDRs (grafting) (EPO 0 239 400; WO 91/09967; and U.S. Pat. Nos. 5,530,101 and 5,585,089), the resurfacing (EPO 0 592 106; EPO 0 519 596; Padlan, 1991, Molec Imm 28(4/5):489-498; Studnicka et al., 1994, Prot Eng 7(6):805-814; and Roguska et al., 1994, PNAS 91:969-973) or chain mixing (U.S. Pat. No. 5,565,332).

The present invention relates in particular to humanized antibodies whose variable parts are modified according to the technology explained in international patent application WO 2009/032661.

This technique notably uses dynamic molecular simulation based on three-dimensional models of antibodies, said models being constructed by homology.

The present invention also relates to any form of antibody having diminished effector functions, such as immunoglobulins bearing mutations of the Fc domain reducing its affinity for the receptors of the immune system or such as nanobodies.

"Effector functions" means any fixation of the Fc domain of the antibody to receptors or proteins inducing immune responses. Decreasing these effector functions makes it possible to reduce adverse effects such as the induction of micro-haemorrhages (Racke et al. J Neurosci 2005, 25:629).

Affinity can be measured by any technique known by a person skilled in the art. It is advantageously measured by the Biostat Speed technique developed on the basis of the algorithms described by Ratkovsk D A and Reedy T J (Biometrics, 1986, 42, 575-82).

In order to permit expression of heavy chains and/or light chains of the antibody according to the invention, the polynucleotides coding for said chains are inserted in expression vectors. These expression vectors can be plasmids, YACs, cosmids, retroviruses, episomes derived from EBV, and all the vectors that a person skilled in the art may judge to be suitable for expression of said chains.

These vectors can be used for transforming cells advantageously derived from one cell line. Said cell line is even more advantageously derived from a mammal. It is advantageously the CHO line or a line derived from this line, or the HEK293 line or a line derived from this line.

The transformation of the cells can be carried out by any method known by a person skilled in the art for introducing polynucleotides into a host cell. Said method can be transformation by means of dextran, precipitation by calcium phosphate, transfection by means of polybrene, protoplast fusion, electroporation, encapsulation of the polynucleotides in liposomes, biolistic injection and direct micro-injection of DNA into the nucleus.

The antibody according to the invention can be included in pharmaceutical compositions with a view to administration by the topical, oral, parenteral, intranasal, intravenous, intramuscular, subcutaneous, intraocular or other routes. Preferably, the pharmaceutical compositions contain pharmaceutically acceptable vehicles for an injectable formulation. These can be in particular sterile, isotonic saline solutions (monosodium or disodium phosphate, sodium, potassium, calcium or magnesium chloride, etc., or mixtures of said salts), or dry compositions, notably lyophilized, which, by adding sterilized water or physiological serum as appropriate, permit injectable solutes to be constituted.

As an example, a pharmaceutical composition comprises (1) a Dulbecco phosphate buffer (pH~7.4), optionally containing 1 mg/ml to 25 mg/ml of human serum albumin, (2) 0.9% w/v of sodium chloride (NaCl), and (3) 5% (w/v) of dextrose. It can also comprise an antioxidant such as tryptamine and a stabilizer such as Tween 20.

The pathologies in question can be any diseases associated with the deposition of amyloid plaques. In particular, the pathology in question is Alzheimer's disease.

The doses depend on the desired effect, the duration of the treatment and the route of administration used; they are generally between 5 mg and 1000 mg of antibody per day for an adult. Generally the doctor will determine the appropriate dosage in relation to the stage of the disease, the patient's age and weight, or any other patient-related factor that has to be taken into account.

The present invention is illustrated, but is not limited, by the examples given below.

EXAMPLES

Example 1

Obtaining Humanized Antibodies

A murine antibody 13C3 was humanized.

This example describes the sequence and the production of the humanized anti-peptide Aβ0 antibody VH1VL1 (LP09027) by production by transient expression in the mammalian line HEK293 designated FreeStyle 293-F.

The cDNAs coding for the humanized variable chains VL1 and VH1 are fused with the cDNAs coding for the human constant regions Ckappa and IgG4 respectively. The sequence of the constant region IgG4 is that of the variant having the substitutions S241 P and L248E in Kabat's nomenclature, for a significant reduction in the production of half-molecules (Angla et al., 1993, Mol. Immunol., 30: 105-108) and the effector functions (WO 97/09351).

Figure 1A:
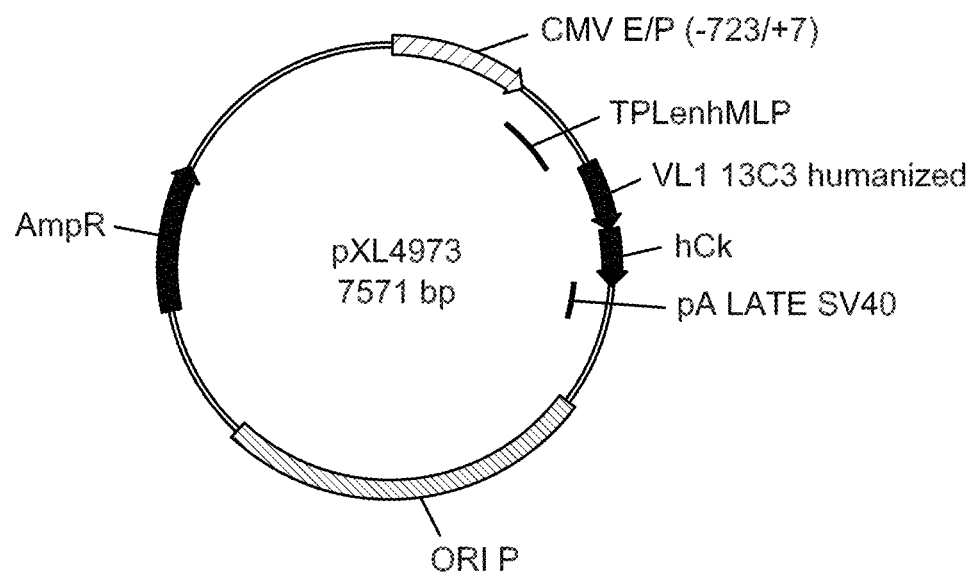
FIG. 1A: Map of the plasmid pXL4973 permitting expression of the light chain LC1 of the antiAbeta antibody 13C3-VH1VL1.
Figure 1B:
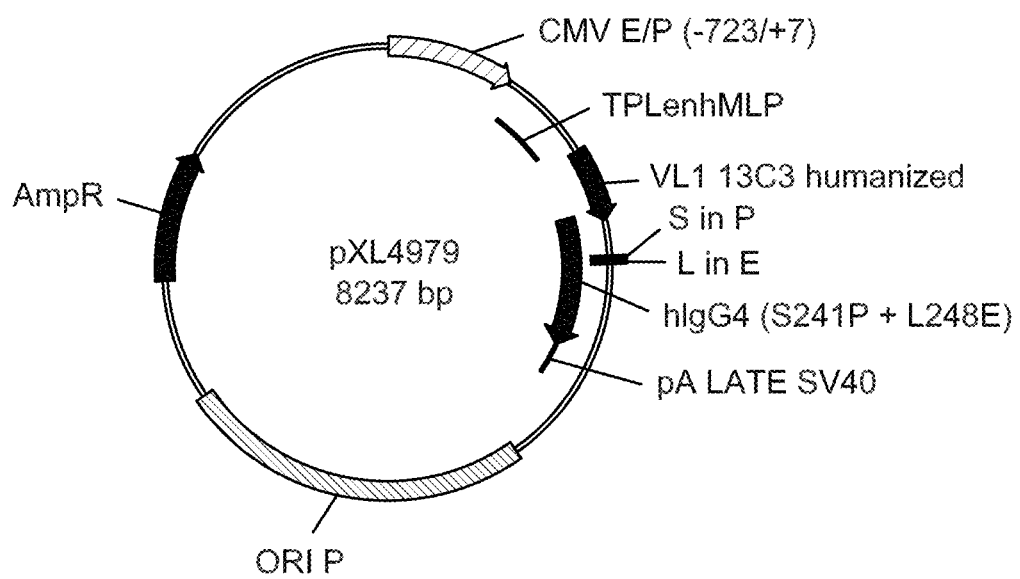
FIG. 1B: Map of the plasmid pXL4979 permitting expression of the heavy chain HC1 of the antiAbeta antibody 13C3-VH1VL1.

The nucleic acid sequences coding for CH1 (SEQ ID NO 1) and for CL1 (SEQ ID NO 3) were cloned independently in the expression vector to generate the plasmids pXL4973 (FIG. 1A) and pXL4979 (FIG. 1B), respectively.

Figure 4A:
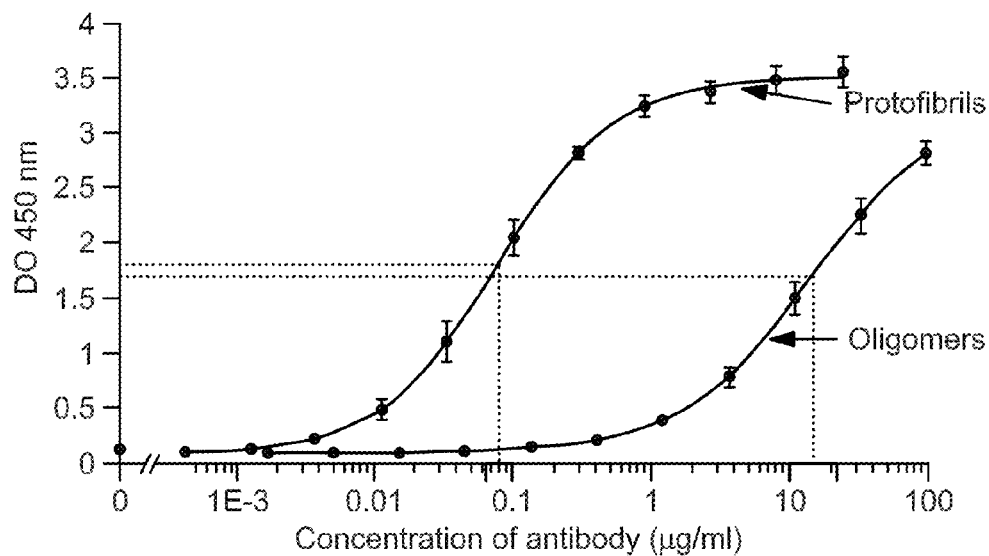
FIGS. 4A, 4B and 4C: Determination of the affinities of the humanized antibodies (antibodies LP09027 (4A), LP09026 (4B) and LP09028 (4C) respectively) for the protofibrils (mean value from 3 experiments ±sem).

A batch of the antibody is produced by production by transient expression in the line FreeStyle 293-F (Invitrogen) after co-transfection of the plasmids pXL4973 and pXL4979 according to the protocol described by Invitrogen (catalogue reference K9000-01). This batch (LP09027) is then purified by affinity chromatography on a column of MabSelect gel (Amersham) according to the supplier's recommendations and then formulated in PBS buffer (reference Dulbecco 14190-094) and submitted to sterile filtration (0.2 µm). Starting from 1 L of culture, 33 mg of antibody is obtained at a purity of 97% by SDS-PAGE in denaturing conditions and by steric exclusion chromatography. The mass obtained by SDS-PAGE in denaturing conditions and by LC/MS is in agreement with the primary amino acid sequence and the presence of an N-glycan on the Fc domain, namely a mass of 23969 Da for LC1 and 49650 Da for HC1 taking into account the N-glycan in the G0F form. The mass obtained by SDS-PAGE in non-denaturing conditions and by size exclusion chromatography is in agreement with the hetero-tetrameric structure of the antibody of 150 kDa (FIG. 4A).

Figure 4B:
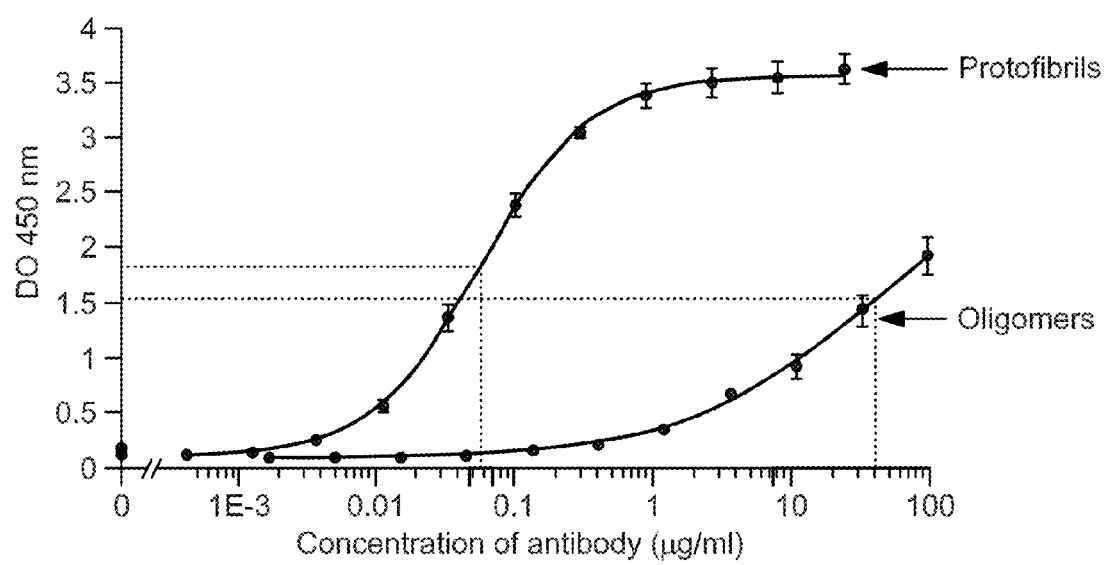
Figure 4C:
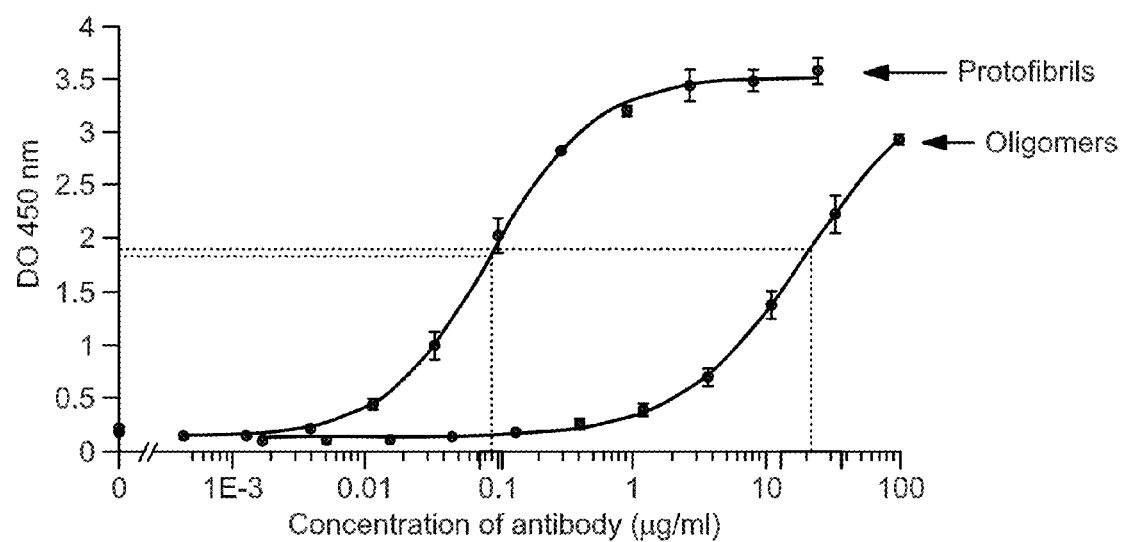

According to the same method, batches of humanized antibodies LP09026 and LP09028 were produced starting from the nucleotide sequences SEQ ID NO 25 and SEQ ID NO 21 for LP09026 (FIG. 4B), and SEQ ID NO 1 and SEQ ID NO 21 for LP09028 (FIG. 4C).

Example 2

Preparation of Protofibrils from Peptide Aβ (1-42)

Figure 2A:
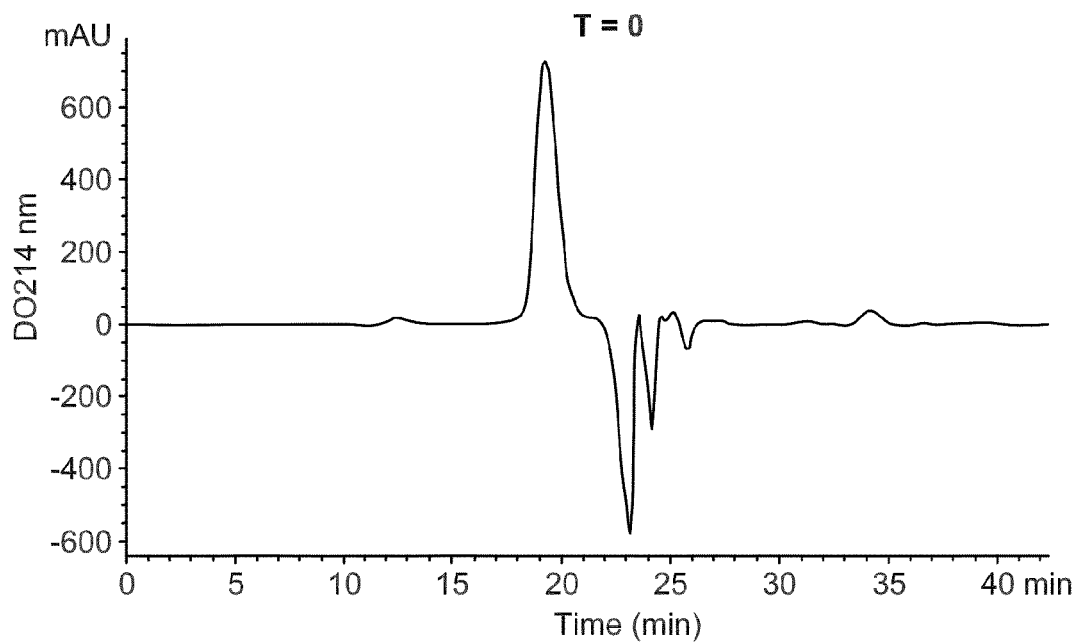
FIGS. 2A and 2B: Separation of the protofibrils and of the low-molecular-weight oligomers by gel filtration on Superdex 75 (at t=0 and at t=16 h respectively).
Figure 2B:
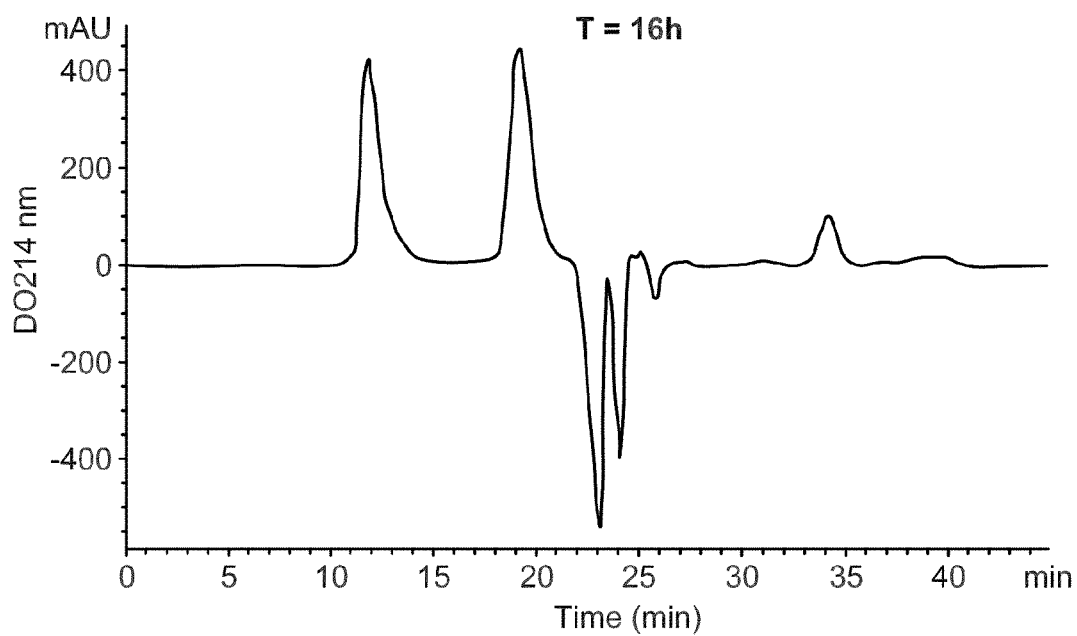
Figure 3:
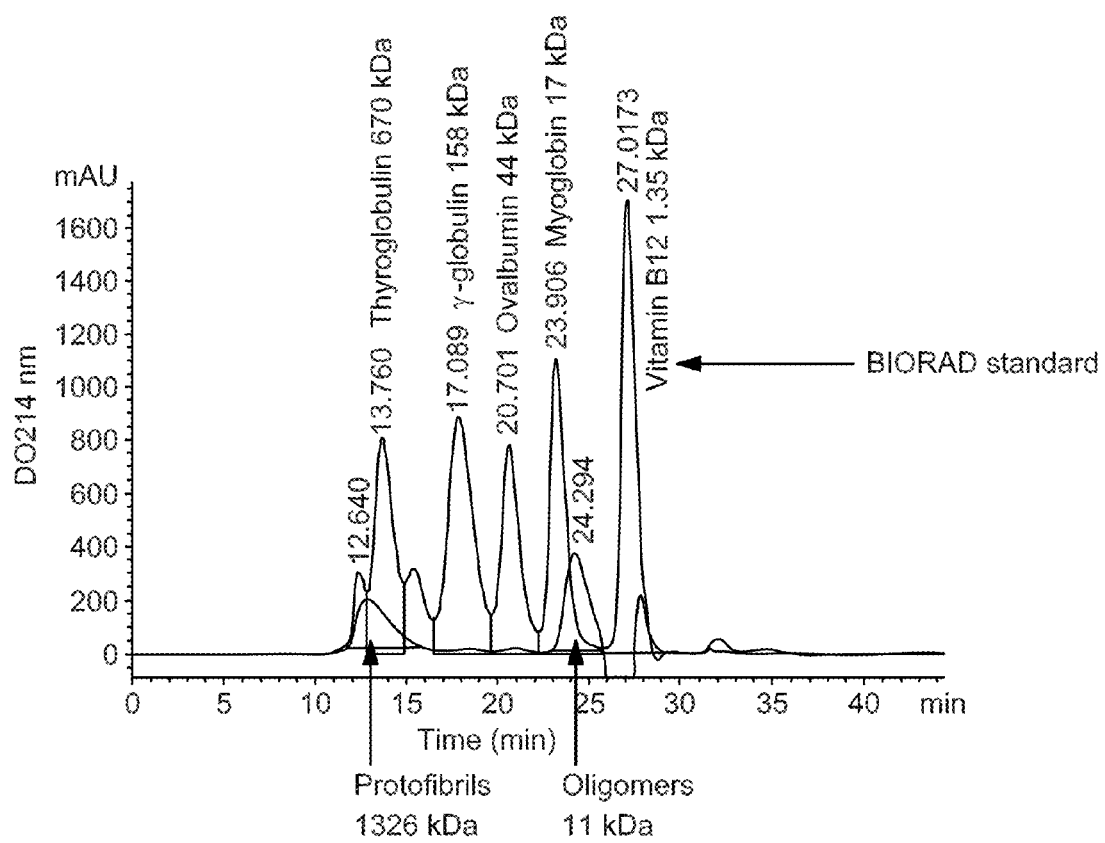
FIG. 3: Determination of the molecular weight of the protofibrils.

The protofibrils were prepared from the synthetic peptide Aβ (1-42) according to the method described by Johansson et al. (FEBS, 2006, 2618-2630). The lyophilized peptide (Anaspec reference 24224) is dissolved in 10 mM NaOH at a concentration of 100 µM, then stirred for 1 min and incubated on ice for 10 min. The solution of peptide is then diluted in buffer of 100 mM sodium phosphate, 200 mM NaCl pH=7.4 to a concentration of 50 µM, then stirred for 1 min. The preparation is incubated overnight at 37° C. for formation of protofibrils and then centrifuged at 17900 g for 15 min at 16° C. to remove the insoluble aggregates. To separate the protofibrils from the oligomeric forms of Aβ of low molecular weight, the supernatant is loaded on a Superdex 75 gel filtration column equilibrated in 50 mM ammonium acetate buffer pH=8.5. The fractions corresponding to the protofibrils and to the low-molecular-weight oligomers are collected and stored at 4° C. FIG. 2 shows a typical profile of separation of the protofibrils. The molecular weight of the protofibrils is determined by Superdex200 gel filtration using, as markers of molecular weight, the Biorad calibration kit (reference 150-1901). FIG. 3 shows that the molecular weight of the protofibrils is greater than 200 kDa.

Example 3

Specificity and Affinity of the Humanized Antibodies with Respect to the Protofibrils 50 µl of protofibrils and low-molecular-weight oligomers at a concentration of 1 µg/ml in PBS (Gibco, reference 70011) are deposited in the wells of an ELISA plate (Nunc, reference 442404) and incubated overnight at 4° C. After removing the excess antigen, 200 µl of buffer PBS+5% milk powder (weight/volume) is deposited in each well to remove the non-specific adsorptions and incubated for 2 h at room temperature. The wells are then washed 4 times with 300 µl of buffer PBS Tween 0.02%. 50 µl of a primary antibody solution (dilution of 3 in 3 in PBS Tween starting from a concentration of 100 µg/ml for the oligomers and from 25 µg/ml for the protofibrils) is added to each well and incubated for 1 h at room temperature. The wells are washed 4 times with 300 µl of buffer PBS Tween. The secondary anti-Fc human antibody coupled to peroxidase (Goat Anti Human IgG (Fc) peroxidase conjugated, Pierce, reference 31413) diluted to 1/10000 in buffer PBS Tween is added to each well and incubated for 1 h at room temperature. After 4 washings with 300 µl of PBS Tween, 100 µl of TMB (Interchim, reference UP664782) is added to each well and incubated for about 10 min, then the reaction is stopped with a solution of 1M HCl (Interchim, reference UPS29590) and the plates are read at an OD measured at a wavelength of 450 nm. The EC50 values are determined by BioStat Speed. The results obtained are presented in Table 1 and in FIG. 4 and show the very high specificity of the antibody for the protofibrils relative to the low-molecular-weight oligomers (factor of 184).

TABLE 1

| EC50 (µg/ml) | LMW | PF | LMW/PF |
| --- | --- | --- | --- |
| LP09026 | 41.4 ± 40.1 | 0.0587 ± 0.004 | 705.3 |
| LP09027 | 14.7 ± 2.7 | 0.0798 ± 0.007 | 184.2 |
| LP09028 | 21.8 ± 5.3 | 0.0892 ± 0.007 | 244.4 |

The lyophilized peptide Aβ1-42 (Anaspec reference 24224) is dissolved according to the supplier's recommendations: 40 µl of 1% NH4OH is added to 500 µg of Aβ1-42. After complete dissolution, 460 µl of PBS is added to obtain a concentration of 1 mg/ml. Aliquots of 10 µl are prepared and stored at −80° C.

50 µl of a solution of peptide Aβ1-42 at a concentration of 1 µg/ml in carbonate buffer (NaHCO$_3$ 0.025 M (Acros Organics, reference 217120010), Na$_2$CO$_3$ 0.025 M (Acros Organics, reference 207810010), pH 9.7 is deposited in the wells of an ELISA plate and incubated overnight at room temperature. As previously, the wells are washed with buffer PBS Tween, incubated in the presence of buffer PBS+5% milk powder (weight/volume) and washed with buffer PBS Tween. The humanized antibody at a concentration of 0.02 µg/ml is incubated for 1 h at room temperature with a concentration range (starting from 1 µg/ml) of peptides Aβ1-28 (Bachem, reference H7865), Aβ1-16 (Anaspec, reference 24225), Aβ25-35 (Anaspec, reference 24227), low-molecular-weight oligomers or protofibrils prepared as described previously. The antibody/antigen mixture is then deposited in each well and the microtitration plate is incubated for 1 h at room temperature. The free, uncomplexed antibody is determined according to the same ELISA protocol as described previously. These competitive experiments show that only the protofibrils with a much higher affinity than the low-molecular-weight oligomers are capable of neutralizing the humanized antibody by preventing it from interacting with the peptide Aβ1-42; none of the peptides is capable of neutralizing the antibody.

Example 4

Specificity of the Humanized Antibody LP09027 with Respect to the Fibrils of Aβ1-42

The peptide Aβ1-42 (Anaspec, 20276) is dissolved in 200 µl of 10 mM NaOH to a concentration of 5 mg/ml. The peptide IAPP (Anaspec, 60804) is diluted in 200 µl of 50% DMSO to a concentration of 5 mg/ml. 100 µl of each preparation is diluted in 400 µl of PBS 1.25×. The final concentration of the peptides is 1 mg/ml in 500 µl. The samples are incubated for 72 h at 37° C. After incubation, the samples are centrifuged at 17900 g for 30 minutes at 4° C. The supernatant is removed and the pellet is washed 3 times with PBS 1×.

Figure 5:
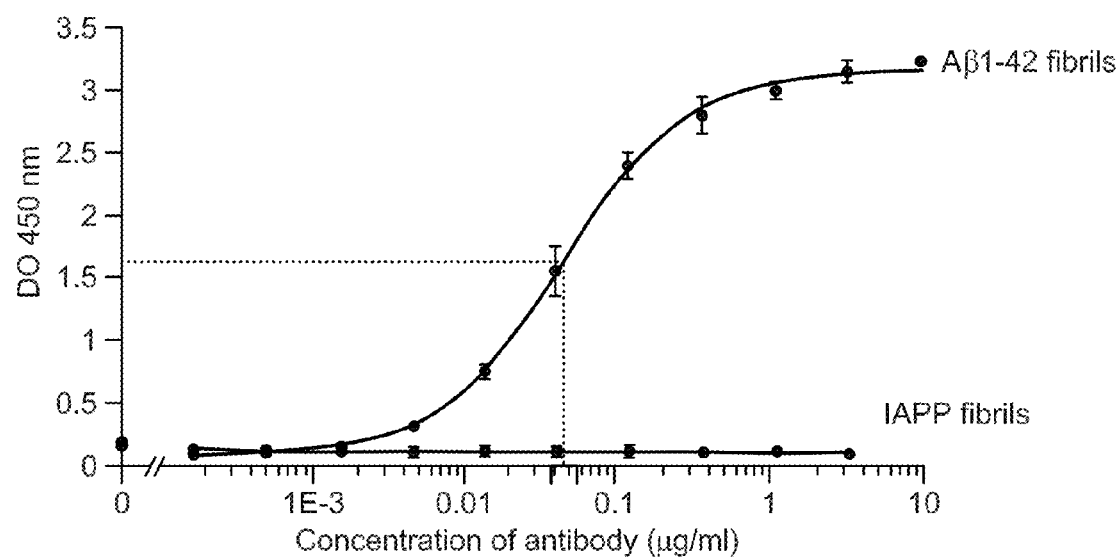
FIG. 5: Specificity of the humanized antibody LP09027 with respect to fibrils of Aft

After the last washing, the pellet of fibrils is taken up in 150 μl of PBS. To check for the presence of fibrils of amyloid type, a thioflavin T fluorescence test (Anaspec, 88306) is carried out. 20 μl of thioflavin T (20 μM final), 10 μl of the sample and 70 μl of PBS 1×(final volume 100 μl) are mixed in a well of a black plate (Corning, 3792). The thioflavin T is excited at 450 nm and, in the presence of a structure of amyloid type, emits fluorescence at 482 nm. 50 μl of fibrils of Aβ1-42 at 1 μg/ml and IAPP at 0.5 μg/ml are deposited in each well of a microtitration plate. The ELISA protocol is applied using serial dilutions of the humanized antibody starting from 10 μg/ml. FIG. 5 shows that the humanized antibody LP09027 specifically recognizes the fibrils of Aβ1-42 but not those of IAPP.

Example 5

Specificity of the Humanized Antibody LP09027 for the Mature Senile Plaques but not for the Diffuse Plaques The humanized antibody (LP09027) conjugated with digoxigenin (digoxigenin-3-O-methylcarbonyl-ε-aminocaproic acid-N-hydroxysuccinimide ester: Roche 11333054001; 11418165001) was used in immunohistochemistry (Ventana Robot) on brain sections from mice APP PS1 (Alzheimer model described by Schmitz C. et al., Am. J. Pathol, 2004, 164, 1495-1502) as well as human brain sections (cerebral cortex) derived from patients with Alzheimer's disease. The samples had been fixed in formol and embedded in paraffin beforehand.

Figure 6A:
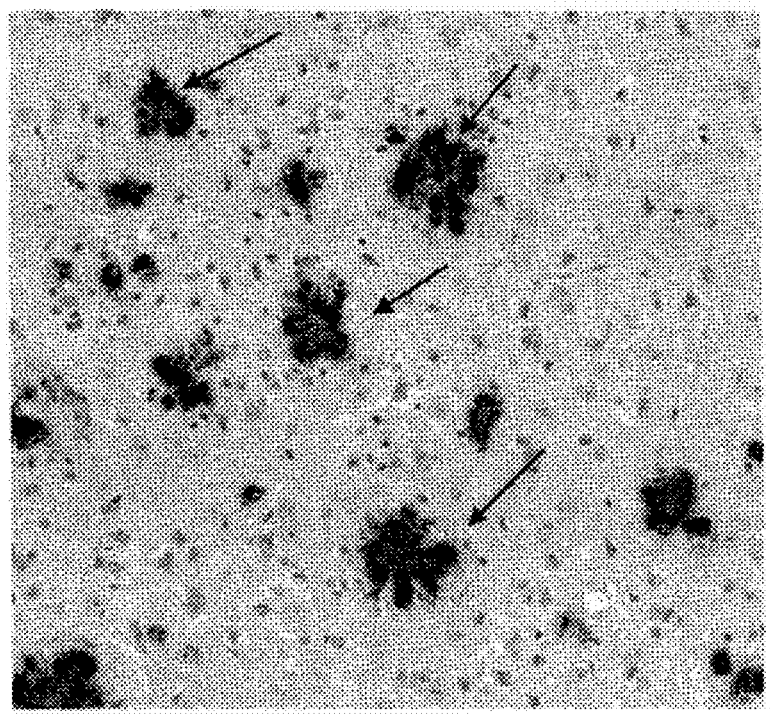
FIGS. 6A and 6B: Specificity of the humanized antibody (LP09027) for the mature senile plaques respectively of the frontal cortex (6A) and of the hippocampus (6B) of a mouse. The arrows indicate the senile plaques.
Figure 6B:
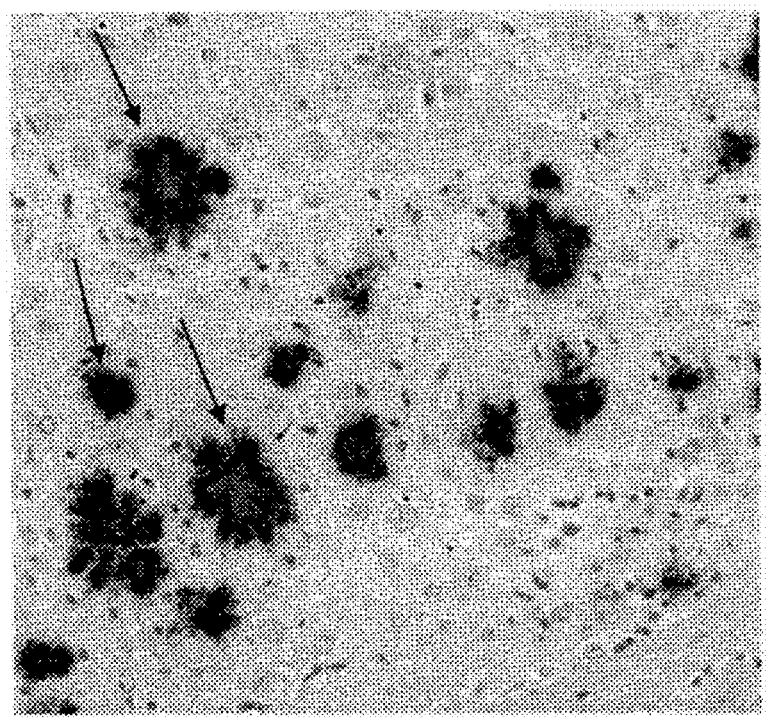

The results obtained in the mouse (FIGS. 6A and 6B) clearly show that the humanized antibody recognizes exclusively the dense, mature senile plaques, but not the diffuse deposits of peptide Aβ.

These data correlate with the properties of this antibody, which is specific for the protofibrillar Abeta form and so does not recognize the soluble, mono- or oligomeric forms of this peptide.

TABLE 2

|  | Nucleotide sequences | Protein sequences |
|---|---|---|
| Antibody 1 VH1VL1 | | |
| $VH_1 + CH_1$ | SEQ ID NO 1 | SEQ ID NO 2 |
| $VL_1 + CL_1$ | SEQ ID NO 3 | SEQ ID NO 4 |
| $VH_1$ | SEQ ID NO 5 | SEQ ID NO 6 |
| $VL_1$ | SEQ ID NO 7 | SEQ ID NO 8 |
| CDR $VH_1$ | SEQ ID NO 9, 11, 13 | SEQ ID NO 10, 12, 14 |
| CDR $VL_1$ | SEQ ID NO 15, 17, 19 | SEQ ID NO 16, 18, 20 |
| Antibody 2 VH1 VL2 | | |
| $VH_1 + CH_1$ | SEQ ID NO 1 | SEQ ID NO 2 |
| $VL_2 + CL_2$ | SEQ ID NO 21 | SEQ ID NO 22 |
| $VH_1$ | SEQ ID NO 5 | SEQ ID NO 6 |
| $VL_2$ | SEQ ID NO 23 | SEQ ID NO 24 |
| CDR $VH_1$ | SEQ ID NO 9, 11, 13 | SEQ ID NO 10, 12, 14 |
| CDR $VL_2$ | SEQ ID NO 31, 17, 19 | SEQ ID NO 32, 18, 20 |
| Antibody 3 VH2 VL2 | | |
| $VH_2 + CH_2$ | SEQ ID NO 25 | SEQ ID NO 26 |
| $VL_2 + CL_2$ | SEQ ID NO 21 | SEQ ID NO 22 |
| $VH_2$ | SEQ ID NO 27 | SEQ ID NO 28 |
| VL2 | SEQ ID NO 23 | SEQ ID NO 24 |
| CDR $VH_2$ | SEQ ID NO 9, 11, 29 | SEQ ID NO 10, 12, 30 |
| CDR $VL_2$ | SEQ ID NO 31, 17, 19 | SEQ ID NO 32, 18, 20 |

The invention claimed is:

1. A method of treatment of Alzheimer's disease, the method comprising administering to a patient a humanized antibody specific for the protofibrillar form of the A-β peptide or a pharmaceutical composition comprising said antibody, wherein said antibody comprises CDRs having the amino acid sequences of SEQ ID NO: 10, 12, 14, 16, 18 and 20, and wherein said antibody is characterized in that the variable region of its heavy chain (VH) comprises a sequence having at least 95% identity with the sequence of SEQ ID NO: 6 and the variable part of its light chain (VL) comprises a sequence having at least 95% identity with the sequence of SEQ ID NO: 8.

2. The method according to claim 1, characterized in that said antibody binds to the A-β peptides aggregated in senile plaques and not to the diffuse deposits of A-β peptides.

3. The method according to claim 1, characterized in that said antibody comprises the CDRs encoded by the nucleotide sequences of SEQ ID Nos: 9, 11, 13, 15, 17 and 19, or by sequences differing respectively by 1, 2, 3, 4 or 5 nucleotides from these sequences.

4. A method of treatment of Alzheimer's disease, the method comprising administering to a patient a humanized antibody specific for the protofibrillar form of the A-β peptide or a pharmaceutical composition comprising said antibody, wherein said antibody comprises CDRs having the amino acid sequences of SEQ ID Nos: 10, 12, 14, 32, 18 and 20.

5. The method according to claim 4, characterized in that said antibody comprises the CDRs encoded by the nucleotide sequences of SEQ ID Nos: 9, 11, 13, 31, 17 and 19, or by sequences differing respectively by 1, 2, 3, 4 or 5 nucleotides from these sequences.

6. A method of treatment of Alzheimer's disease, the method comprising administering to a patient a humanized antibody specific for the protofibrillar form of the A-β peptide or a pharmaceutical composition comprising said antibody, wherein said antibody comprises CDRs having the amino acid sequences of SEQ ID Nos: 10, 12, 30, 32, 18 and 20.

7. The method according to claim 6, characterized in that said antibody comprises the CDRs encoded by the nucleotide sequences of SEQ ID Nos: 9, 11, 29, 31, 17 and 19, or by sequences differing respectively by 1, 2, 3, 4 or 5 nucleotides from these sequences.

8. The method according to claim 4, characterized in that said antibody comprises a variable region of a heavy chain (VH) comprising a sequence having at least 80% identity with the sequence of SEQ ID NO: 6.

9. The method according to claim 4, characterized in that said antibody comprises a heavy chain comprising the amino acid sequence of SEQ ID NO: 6.

10. The method according to claim 1, characterized in that said antibody comprises a light chain comprising the amino acid sequence of SEQ ID NO: 8.

11. The method according to claim 1, characterized in that the amino acid sequence of said antibody comprises the amino acid sequences of SEQ ID Nos: 6 and 8.

12. The method according to claim 1 or 4, characterized in that said antibody comprises a heavy chain having at least 80% identity with the amino acid sequence of SEQ ID NO: 2.

13. The method according to claim 1, characterized in that said antibody comprises a light chain having at least 80% identity with the amino acid sequence of SEQ ID NO: 4.

14. The method according to claim 1, characterized in that the sequence of said antibody comprises the amino acid sequences of SEQ ID Nos: 2 and 4.

15. The method according to claim 4, characterized in that the sequence of said antibody comprises the amino acid sequences of SEQ ID Nos: 6 and 24.

16. The method according to claim 6, characterized in that the sequence of said antibody comprises the amino acid sequences of SEQ ID Nos: 28 and 24.

17. The method according to claim 1, 4 or 6, characterized in that said antibody induces a reduction of amyloid plaques.

18. The method according to claim 1, 4 or 6, characterized in that the affinity of said antibody for the protofibrillar form of peptide A-β is at least 100 times greater than its affinity for the other forms of the peptide.

19. The method according to claim 4 or 6, characterized in that said antibody comprises a variable region of a light chain (VL) comprising a sequence having at least 80% identity with the amino acid sequence of SEQ ID NO: 24.

20. The method according to claim 4 or 6, characterized in that said antibody comprises a light chain comprising the amino acid sequence of SEQ ID NO: 24.

21. The method according to claim 4 or 6, characterized in that said antibody comprises a light chain having at least 80% identity with the amino acid sequence of SEQ ID NO: 22.

22. The method according to claim 4, characterized in that the sequence of said antibody comprises the amino acid sequences of SEQ ID Nos: 2 and 22.

23. The method according to claim 6, characterized in that said antibody comprises a variable region of a heavy chain (VH) comprising a sequence having at least 80% identity with the amino acid sequence of SEQ ID NO: 28.

24. The method according to claim 6, characterized in that said antibody comprises a heavy chain comprising the amino acid sequence of SEQ ID NO: 28.

25. The method according to claim 6, characterized in that said antibody comprises a heavy chain having at least 80% identity with the amino acid sequence of SEQ ID NO: 26.

26. The method according to claim 6, characterized in that the sequence of said antibody comprises the amino acid sequences of SEQ ID Nos: 26 and 22.

* * * * *